United States Patent
Marin et al.

(10) Patent No.: US 10,993,868 B2
(45) Date of Patent: May 4, 2021

(54) DYNAMIC FOOT PLATE

(71) Applicant: MDPO LLC, Sunrise, FL (US)

(72) Inventors: Luis E. Marin, Sunrise, FL (US); Steve Ward, Miami, FL (US)

(73) Assignee: MDPO LLC, Sunrise, FL (US)

( * ) Notice: Subject to any disclaimer, the term of this patent is extended or adjusted under 35 U.S.C. 154(b) by 1266 days.

(21) Appl. No.: 15/167,158

(22) Filed: May 27, 2016

(65) Prior Publication Data

US 2021/0100714 A1    Apr. 8, 2021

Related U.S. Application Data

(63) Continuation-in-part of application No. 14/716,286, filed on May 19, 2015, now Pat. No. 10,463,522, which is a continuation-in-part of application No. 14/099,177, filed on Dec. 6, 2013, now abandoned.

(60) Provisional application No. 62/168,287, filed on May 29, 2015, provisional application No. 61/782,286, filed on Mar. 14, 2013.

(51) Int. Cl.
*A61B 17/64* (2006.01)
*A61H 1/02* (2006.01)

(52) U.S. Cl.
CPC .......... *A61H 1/0266* (2013.01); *A61B 17/64* (2013.01)

(58) Field of Classification Search
CPC ...................... A61B 17/60–666; A61H 1/0266
See application file for complete search history.

(56) References Cited

U.S. PATENT DOCUMENTS

| | | | |
|---|---|---|---|
| 2,020,262 A | 11/1935 | Longfellow | |
| 2,035,952 A | 3/1936 | Ettinger | |
| 2,079,567 A | 5/1937 | Anderson | |
| 2,393,831 A | 1/1946 | Stader | |
| 2,406,987 A | 9/1946 | Anderson | |
| 3,941,123 A | 3/1976 | Volkov et al. | |
| 4,176,627 A | 12/1979 | Bassi | |
| 4,308,863 A | 1/1982 | Fischer | |
| 4,338,927 A | 7/1982 | Volkov et al. | |
| 4,450,834 A * | 5/1984 | Fischer ................. | A61B 17/62 606/102 |
| 4,535,763 A | 8/1985 | Jacquet | |

(Continued)

FOREIGN PATENT DOCUMENTS

| | | |
|---|---|---|
| EP | 2194881 | 11/2016 |
| RU | 2391931 | 6/2010 |

(Continued)

*Primary Examiner* — Nicholas J Plionis
(74) *Attorney, Agent, or Firm* — Malloy & Malloy, P.L.

(57) ABSTRACT

A dynamic foot plate assembly structured for therapeutic use adjacent the ankle area of the body comprising a base element, at least one side element extending along the ankle area, and at least one joint movably and adjustably connecting the base element to the side element for variable displacement of the base element and side element into different operative orientations. The dynamic foot plate assembly may also comprise a plurality of strut members disposed in an interconnecting relationship between either a support member and a side element, or the support member and the base element. The strut members, if present, facilitate the variable relative displacement of the base element, side element and support element into different operative orientations.

15 Claims, 18 Drawing Sheets

(56) References Cited

U.S. PATENT DOCUMENTS

| | | | |
|---|---|---|---|
| 4,607,625 A | 8/1986 | Schenck | |
| 4,624,249 A | 11/1986 | Alvarez Cambras | |
| 4,696,293 A | 9/1987 | Ciullo | |
| 4,768,524 A | 9/1988 | Hardy | |
| 5,062,844 A | 11/1991 | Jamison et al. | |
| 5,067,954 A | 11/1991 | Ilizarov | |
| 5,087,258 A | 2/1992 | Schewior | |
| 5,139,498 A | 8/1992 | Astudillo Ley | |
| 5,358,504 A * | 10/1994 | Paley | A61B 17/66 606/105 |
| 5,468,242 A | 11/1995 | Reisberg | |
| 5,496,319 A | 3/1996 | Allard et al. | |
| 5,540,686 A | 7/1996 | Zippel et al. | |
| 5,578,041 A | 11/1996 | Nash et al. | |
| 5,681,309 A | 10/1997 | Ross, Jr. et al. | |
| 5,702,389 A | 12/1997 | Taylor et al. | |
| 5,743,898 A | 4/1998 | Bailey et al. | |
| 5,776,132 A | 7/1998 | Blyakher | |
| 5,788,695 A | 8/1998 | Richardson | |
| 5,814,048 A | 9/1998 | Morgan | |
| 5,891,143 A | 4/1999 | Taylor et al. | |
| 5,931,837 A | 8/1999 | Marsh et al. | |
| 6,030,386 A * | 2/2000 | Taylor | A61B 17/62 606/54 |
| 6,328,737 B1 | 12/2001 | Moorcroft et al. | |
| 6,355,037 B1 | 3/2002 | Crosslin et al. | |
| 6,461,358 B1 | 10/2002 | Faccioli et al. | |
| 6,964,663 B2 | 11/2005 | Grant et al. | |
| 7,025,790 B2 | 4/2006 | Parks et al. | |
| 7,048,735 B2 | 5/2006 | Ferrante et al. | |
| 7,189,237 B2 | 3/2007 | Huebner | |
| 7,361,176 B2 | 4/2008 | Cooper et al. | |
| 7,422,593 B2 | 9/2008 | Cresina et al. | |
| 7,806,843 B2 | 10/2010 | Marin | |
| 7,887,498 B2 | 2/2011 | Marin | |
| 8,251,937 B2 | 8/2012 | Marin | |
| 8,439,914 B2 | 5/2013 | Ross et al. | |
| 9,924,968 B2 | 3/2018 | Marin | |
| 10,463,522 B2 | 11/2019 | Marin | |
| 2002/0010465 A1 | 1/2002 | Koo et al. | |
| 2004/0059331 A1* | 3/2004 | Mullaney | A61B 17/6458 606/59 |
| 2004/0138659 A1 | 7/2004 | Austin et al. | |
| 2004/0167530 A1 | 8/2004 | Hamel | |
| 2005/0149018 A1 | 7/2005 | Cooper et al. | |
| 2005/0251135 A1 | 11/2005 | Riccione et al. | |
| 2007/0055234 A1 | 3/2007 | McGrath et al. | |
| 2007/0161984 A1 | 7/2007 | Cresina et al. | |
| 2007/0255280 A1 | 11/2007 | Austin et al. | |
| 2008/0021451 A1* | 1/2008 | Coull | A61B 17/62 606/54 |
| 2009/0082709 A1 | 3/2009 | Marin | |
| 2009/0105621 A1 | 4/2009 | Boyd et al. | |
| 2009/0177197 A1 | 7/2009 | Marin | |
| 2009/0275944 A1 | 11/2009 | Huebner et al. | |
| 2010/0179548 A1 | 7/2010 | Marin | |
| 2010/0234844 A1 | 9/2010 | Edelhauser et al. | |
| 2010/0234896 A1 | 9/2010 | Lorenz et al. | |
| 2010/0312243 A1* | 12/2010 | Ross | A61B 17/62 606/56 |
| 2010/0331840 A1* | 12/2010 | Ross | A61B 17/6475 606/54 |
| 2012/0209163 A1 | 8/2012 | Phillips | |
| 2012/0330312 A1 | 12/2012 | Burgherr et al. | |
| 2014/0257287 A1 | 9/2014 | Chang et al. | |
| 2014/0276260 A1 | 9/2014 | Marin | |
| 2015/0032107 A1 | 1/2015 | Marin | |
| 2015/0282973 A1 | 10/2015 | Marin | |

FOREIGN PATENT DOCUMENTS

| | | |
|---|---|---|
| WO | WO 2007/067297 | 6/2007 |
| WO | WO 2007/111576 | 10/2007 |
| WO | WO 2009/042167 | 4/2009 |
| WO | WO 2010/083033 | 7/2010 |
| WO | WO 2014/152559 | 9/2014 |
| WO | 2016196498 A1 | 12/2016 |

* cited by examiner

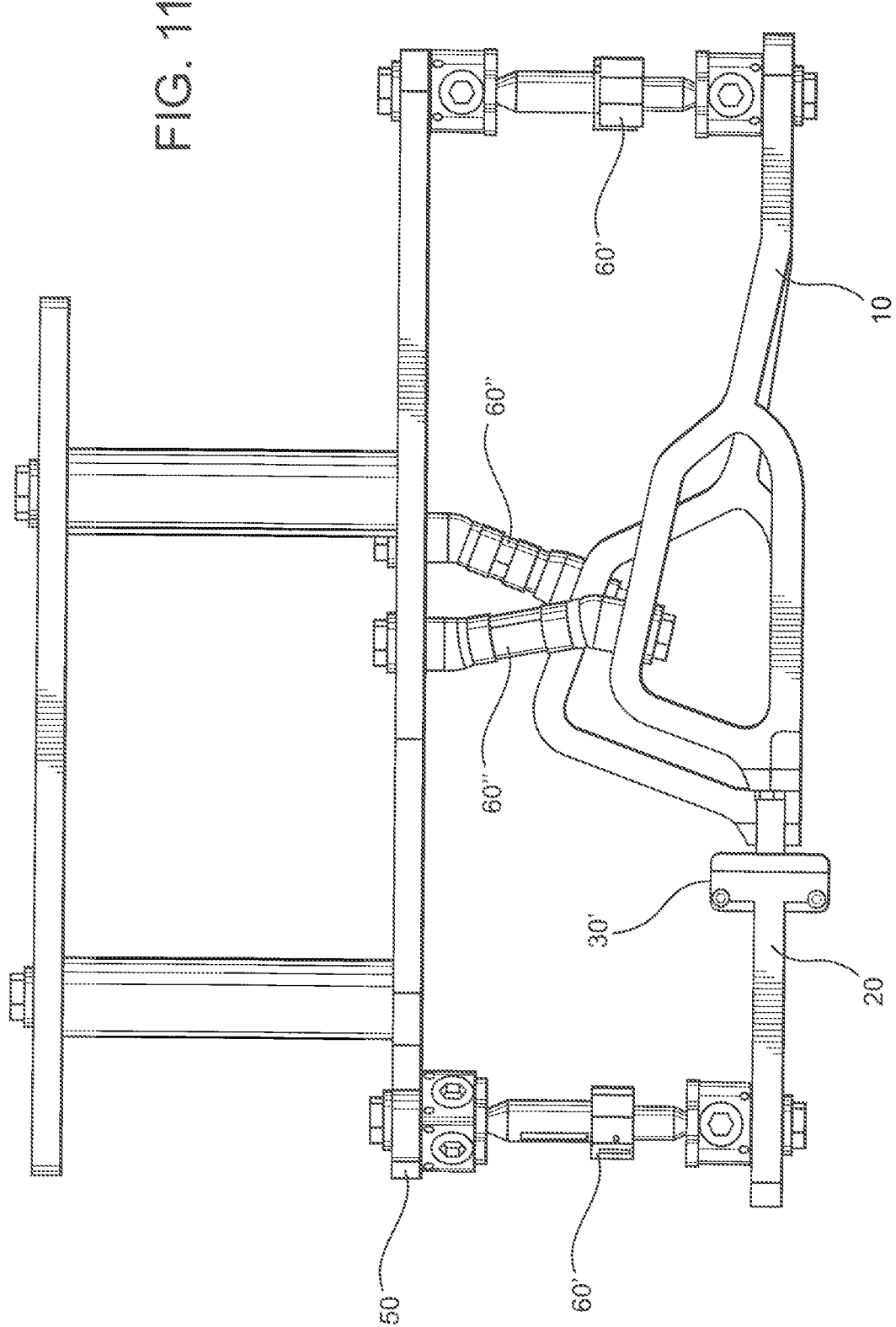

DYNAMIC FOOT PLATE

CLAIM OF PRIORITY

The present application claims priority under 35 U.S.C. § 119(e) to a provisional patent application having Ser. No. 62/168,287, filing on May 29, 2015, Additionally, this Application claims priority to continuation-in-part patent application having Ser. No. 14/716,286, filed on May 19, 2015, which matured into U.S. Pat. No. 10,463,522 on Nov. 5, 2019, which claims priority to application having Ser. No. 14/099,177, filed on Dec. 6, 2013 which also claims priority under 35 U.S.C. § 119(e) to a provisional patent application filed with the U.S. Patent Office on Mar. 14, 2013, and assigned Ser. No. 61/782,286, incorporated herein by reference.

BACKGROUND OF THE INVENTION

Field of the Invention

This invention is directed to a support assembly for use in operative placement relative to and treatment of the ankle area including the ankle joint, foot and correspondingly disposed lower leg bones. The assembly allows for a variable orientation of at least one of its members, at least one of which is structured for the disposition of at least one transfixion pin for the engagement and treatment of a patient's ankle area.

Description of the Related Art

In the medical treatment of pathologies including, but not limited to, injuries, fractures, etc. to the bone and joints, external fixator assemblies are commonly used to maintain segments of the bone in an intended and/or required stabilized orientation. By way of example, fixator assemblies of the type described may be utilized to treat the fusion of bone tissue as well soft tissue injuries, and situations involving a union of bones which otherwise are difficult to heal. As such, known or conventional fixator assemblies vary in structure, dimension and configuration and are correspondingly adapted to be used with various portions of the body to which they are attached.

Typical fixator structures include at least one connecting bar or rod as well a plurality of clamps for adjustably securing fixation pins, wires, etc. to the bone portions being affected. Further, transfixion pins or wires of the types commonly utilized may extend completely through the bony tissue or may be anchored therein, such as when the long bones of the leg are involved directly or indirectly with the treatment or healing procedure. Further, the term "transfixion member" is generally recognized in the medical field as including the describing of elongated pins which extend completely or at least partially through the bony tissue involved. In contrast, smaller, thicker "half pins" may be utilized in substantially the same manner to stabilize affected tissue but being of a length insufficient to extend completely through the affected bone, joint, etc. This term may also be used in a more generic sense in referring to stabilizing devices, other than pins, such as wires, reduction wires, screws, clamps, etc.

In addition, known external fixator assemblies of the type described may also include support rings which encircle a corresponding body member, wherein such rings or like support elements serve as a supportive base to facilitate proper location of the aforementioned transfixion members. Accordingly, it is commonly understood in the medical profession that fixator assemblies are used to maintain proper orientation of one or more of bones or bone segments relative to one another to facilitate healing or alignment.

However, the proper stabilization of tissue typically associated with the joint areas of a patient's body such as, but not limited to, the ankle joint as well as the wrist and other smaller bones associated with the hand involves additional considerations.

It would therefore be beneficial to implement a technology that incorporates dynamic aspects to allow for the acute and/or gradual relocation of a foot, ankle or leg deformity. With the dynamic properties of the assembly, a foot, ankle or leg soft tissue and bony pathology can be corrected. In addition, the calibration of the movable components of the assembly allows for ease of use and increased accuracy of adjustments, allowing the surgeon to correct complicated deformities.

SUMMARY OF THE INVENTION

This invention is directed to a dynamic foot plate assembly primarily, but not exclusively, structured for placement adjacent an ankle area of the body. As referred to herein, the term "ankle area" is intended to describe the ankle joint, as well as bones and associated tissue of the foot and lower portions of the leg including the fibula and tibia. Further, in properly describing the intended position and orientation of the various preferred embodiments of the external fixator assembly of the present invention, terminology including "length of the ankle area" and/or "height of the ankle area" may be utilized synonymously. These terms are meant to refer to the general distance between the bottom of the foot and an area of the lower part of the leg above the ankle joint. Further the ankle area, as used herein, is meant to be descriptive of the bones and other tissue associated with the foot, ankle joint and lower leg which serve to facilitate the functioning of the ankle joint and intended, relative movements of the corresponding foot and leg connected to the ankle joint.

Accordingly, the dynamic foot plate assembly includes a configuration of side elements and joints connected to a base element intended to be disposed adjacent to the ankle area. The side elements are structured to support at least one transfixion pin or like transfixion member in operative engagement with the bones or other associated tissue of the ankle area. Consequently, the assembly includes at least one base segment preferably, but not necessarily, having a curvilinear configuration substantially in the form of an arc and or/semi-circle operatively disposed at the medial and lateral longitudinal segments.

In addition, the assembly includes a configuration of joints and side elements attached to the base element and extending transversely from the base element and adjacent the ankle area. The joints and side elements are movably connected and structured to allow variable disposition of the side elements relative to the base element, including but not limited to rotation, raising/lowering, hinging/tilting, and varying the longitudinal spacing/telescoping of the configuration. Some joints may be further capable of being locked or fixed, allowing for the configuration of joints and side elements to become fixed relative to one another. Joints can subsequently be unlocked, restoring the ability for the configuration to once again be articulated.

Further, at least one strut member, which may work in concert with at least one joint, extends from a support member, disposed adjacent the ankle and above the base element, and can be connected to either a base element or a side element to allow for the relative disposition of the dynamic foot plate array into a desired orientation for treatment.

One embodiment of the present invention comprises a base element, as previously described, movably interconnected to two joints, each disposed on an opposing side of the ankle, which are in turn movably interconnected to a pair of side elements extending substantially transversely to the base along opposing sides of the ankle. A pair of strut members are structured to movably interconnect the base element to a support member disposed adjacent to the ankle. A second pair of strut members are structured to movably interconnect the support member to the aforementioned side elements. The four strut members and two joints are structured to cooperatively dispose the base element, side elements and support member into a desired orientation for treatment of the ankle and related areas of the lower leg.

Yet another preferred embodiment of the present invention is directed to an adjustable joint assembly which is usable on the dynamic footplate and/or other parts of external fixator devices. More specifically, at least one or more practically a plurality of the adjustable joint assemblies are structured to position components, such as the struts, through different adjustment modes. Moreover, the different adjustment modes include, but are not limited to, a gross adjustment mode and a fine adjustment mode. Further, the component of the external fixator device and/or footplate, which is connected to the joint assembly may include a strut, of the type referred to in detail herein. As such, the strut component is disposed to connect a support device in a proper orientation, typically above the dynamic footplate and in a preferred aligned with the limb of the patient being treatment.

As used herein, the term "gross adjustment mode" and "fine adjustment mode" respectively refer, at least in part, to a major adjustable positioning and minor, fine adjustable positioning of the strut or other component. As such, the gross adjustment mode refers to greater range of motion of the strut or component so as to accommodate assembly, initial positioning, alignment, etc. of the various components of the external fixator relative to the footplate or other portions of the external fixator device. In contrast, the fine adjustment mode refers to a smaller or lesser range of motion through which the strut or component may be adjustably disposed, in order to accomplish a more precise position or orientation of the strut or component. In addition, the fine adjustment mode may be used to more precisely position the connected component or strut, once the external fixator has been assembled and initially disposed and aligned, but perhaps not perfectly or preferably oriented.

Accordingly, as utilized and embodied in an external fixator device, at least one joint assembly, but possibly a plurality of joint assemblies, may be disposed on a housing. As such, each of one or more joint assemblies includes a primary adjustment assembly and a secondary adjustment assembly, each movably disposed on the housing. Further, the housing may be disposed on the footplate, support plate, or other portions of the external fixator device. As will be apparent hereinafter, a plurality of such housings each including one or more joint assemblies may be located on different portions of the footplate, support plate, etc. to facilitate proper adjustable positioning or orientation of the struts or other components to which the one or more joint assemblies are connected.

Each primary adjustment assembly is disposed and structured to movably adjust the strut or other component through first range of motion, wherein the secondary adjustment assembly is disposed and structured to movably adjust the strut or component through second range of motion. Further, a lock assembly is associated with each joint assembly and is disposable into and out of movement restricting relation to a corresponding primary adjustment assembly. Such movement restricting relation will serve to restrict movement of the primary adjustment assembly through the aforementioned first range of motion. However, the lock assembly may be incorporated within and be at least partially defined by the aforementioned secondary adjustment assembly.

As a result of the inclusion and/or integration of the lock assembly with the secondary adjustment assembly, movement of the lock assembly and corresponding portions of the second adjustment assembly into the movement restricting relation will still allow and/or facilitate the aforementioned fine adjustment of the strut or component through manipulation of the lock assembly/secondary adjustment assembly. Therefore, the aforementioned first range of motion of the component or strut, accomplished by the primary adjustment assembly, represents a "gross adjustment mode" thereof. In contrast, the aforementioned second range of motion of the secondary adjustment assembly/lock assembly is representative of the aforementioned "fine adjustment mode" of the strut or component.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 11 is a side view of the embodiment of FIG. 9.

Like reference numerals refer to like parts throughout the several views of the drawings.

DETAILED DESCRIPTION OF THE PREFERRED EMBODIMENT

Figure 10:
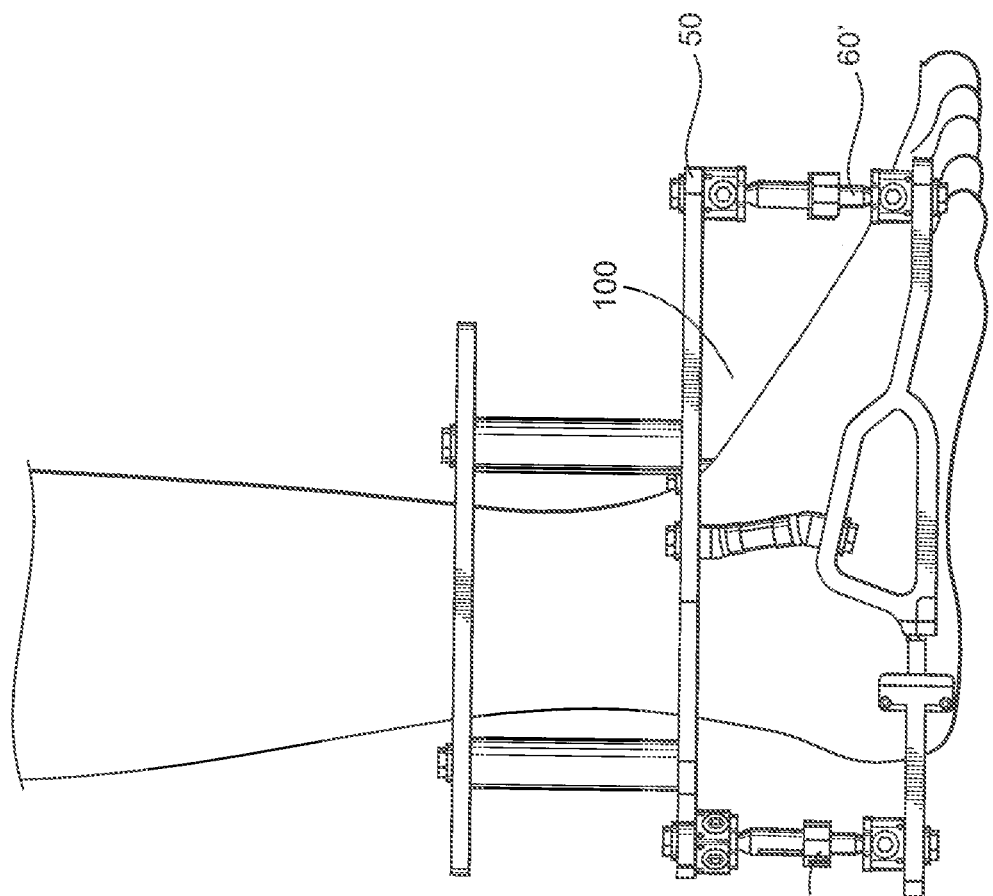
FIG. 10 is a side view of the embodiment of FIG. 9 when operatively positioned relative to an ankle area of a patient.
Figure 9:
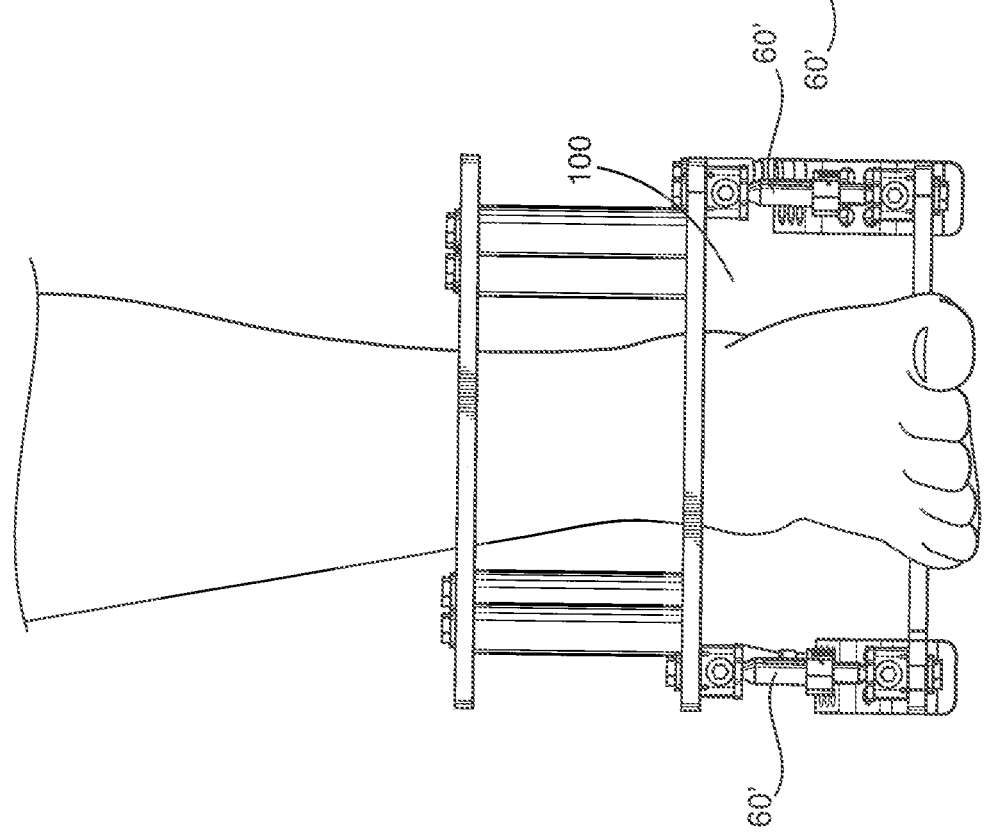
FIG. 9 is a front view of another preferred embodiment of the present invention when operatively positioned relative to an ankle area of a patient.

As represented in the accompanying figures, the present invention is directed to a dynamic foot plate assembly generally indicated as 1. As demonstrated the dynamic foot plate assembly 1 is structured to be operatively positioned and used in a location substantially adjacent the ankle area 100 of a patent as indicated in FIGS. 9 and 10. As set forth above, the ankle area 100 is meant to be descriptive of substantially the entire area, which includes the ankle joint, foot, corresponding portions of the leg bones, including the fibula and tibia, as well as the associated components and tissue. In addition, the terms "height" and "length" of the ankle area 100 are used synonymously herein and refer to the distance from substantially the bottom of the foot, to at least a portion of the long bones of the leg.

Figure 6:
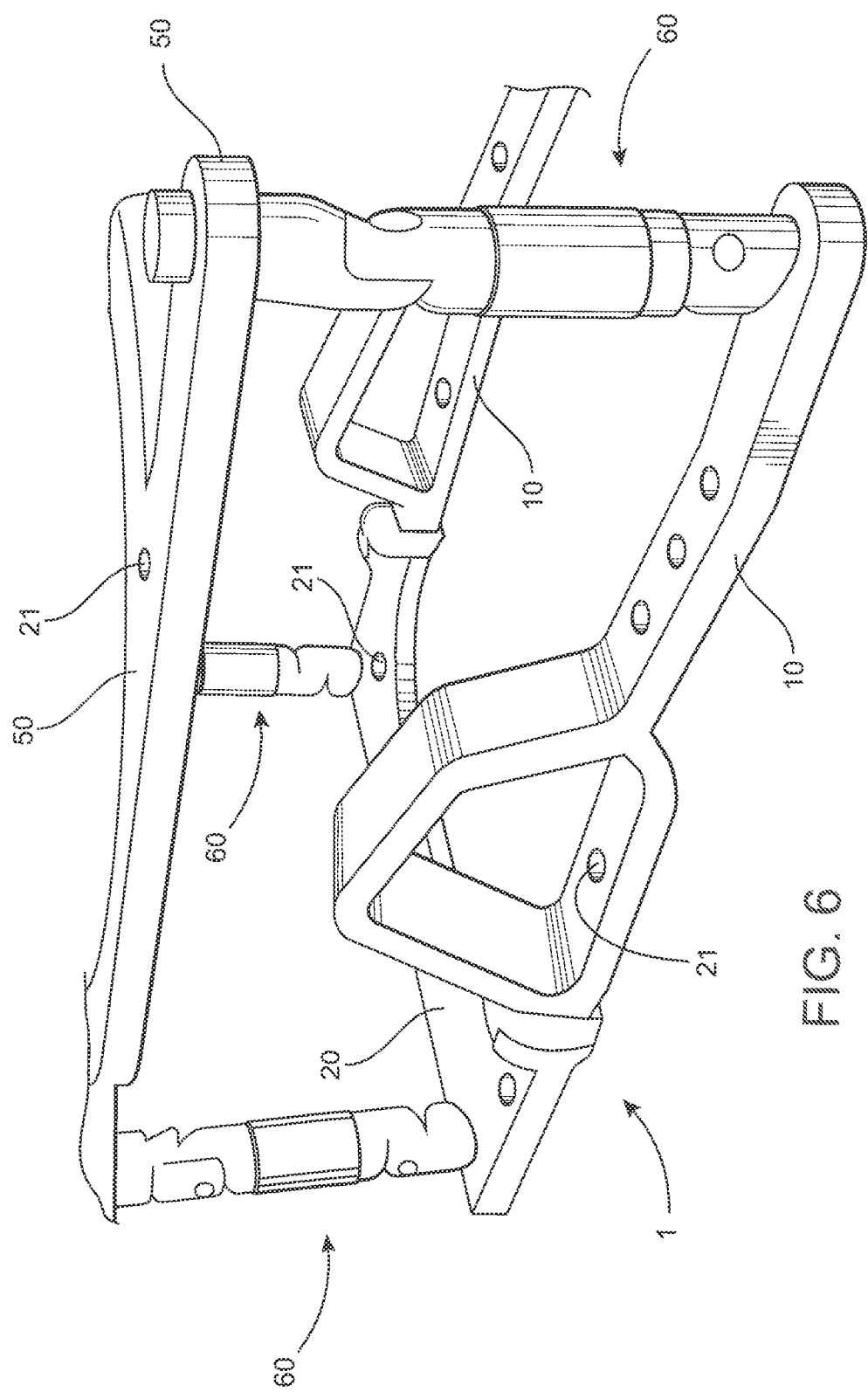
FIG. 6 is a side perspective view in partial cutaway of a plurality of strut members which may be operatively associated with the preferred embodiment of FIG. 1.

Accordingly, the dynamic foot plate assembly 1 comprises a base element generally indicated as 20 movably interconnected to at least one joint generally indicated as 30. In FIG. 11, a possible alternate embodiment of a joint is given at 30'. With reference to FIG. 6, additionally, the foot plate assembly 1 further comprises at least one strut member generally indicated as 60 interconnected to at least one support member generally indicated as 50 and at least one side element generally indicated as 10. With primary reference to FIG. 1, the base element 20 defining at least a portion of the dynamic foot plate assembly 1 in the preferred embodiment includes a curvilinear configuration which may be more specifically defined by an arcuate or semi-circular shape, but other suitable shapes will suffice. As such, the base element 20 terminates in oppositely disposed free ends 22. Further, a plurality of apertures 21 or other appropriate structure are positioned substantially along the length of the base element 20, at least one side element 10, and the support member 50, and are provided to facilitate connection of at least one fixation strut preferably using fixation bolts, which are not shown for purposes of clarity. Such struts and interconnecting fixation bolts are used to support and/or dispose the base segment 20 in a stabilized position relative to the ankle area 100. The opposite ends of such struts, to which the base element 20 is connected, may be secured to a halo-type ring located above the ankle area 100 along the length of the leg and in surrounding relations to the bones of the leg. Such anchoring of the halo ring provides stabilizing support to the base element 20 by virtue of the interconnection between the halo ring and the base element 20 by the plurality of strut members 60.

Figure 1:
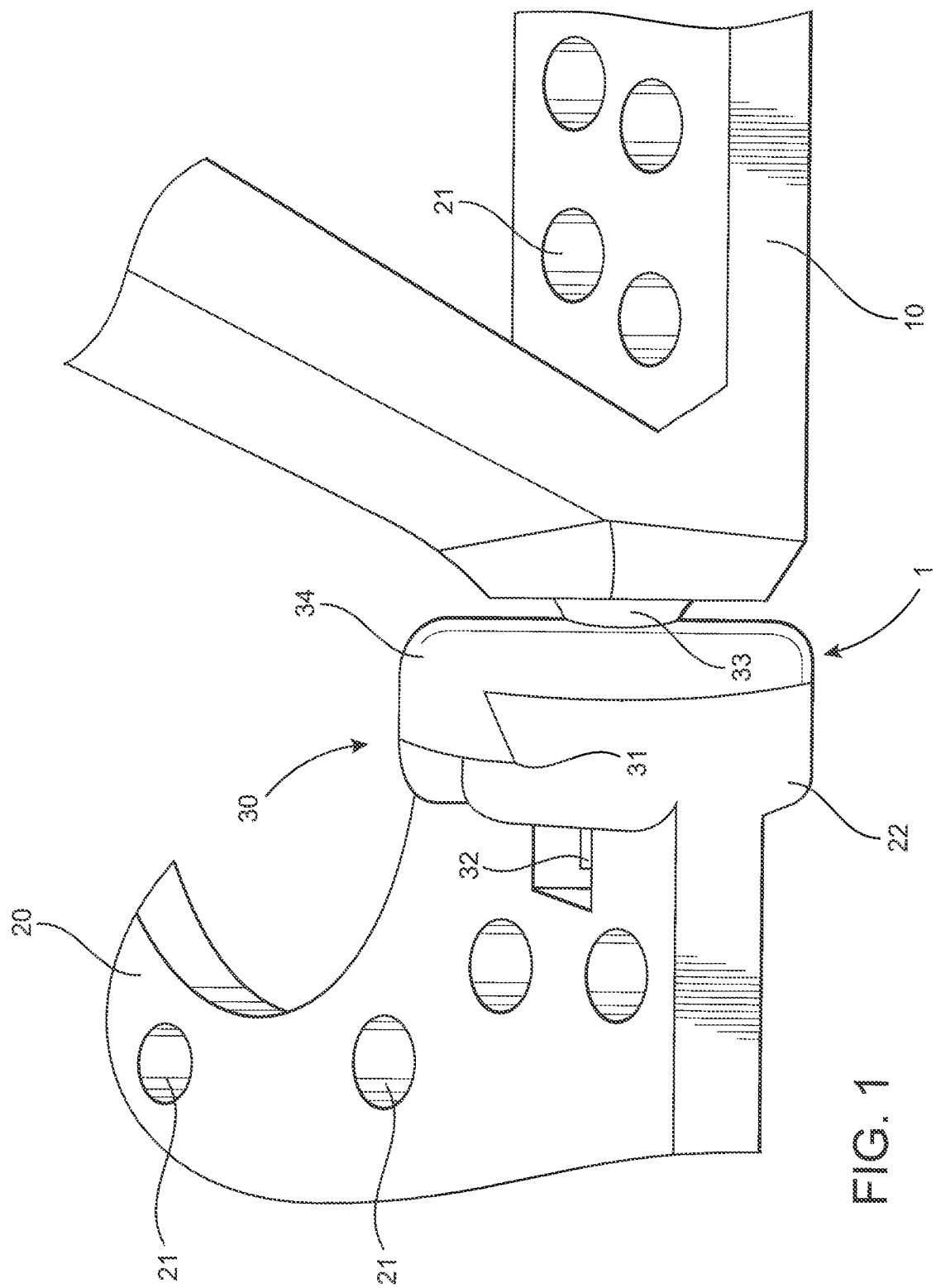
FIG. 1 is a side perspective view in partial cutaway of one preferred embodiment of the present invention.
Figure 2:
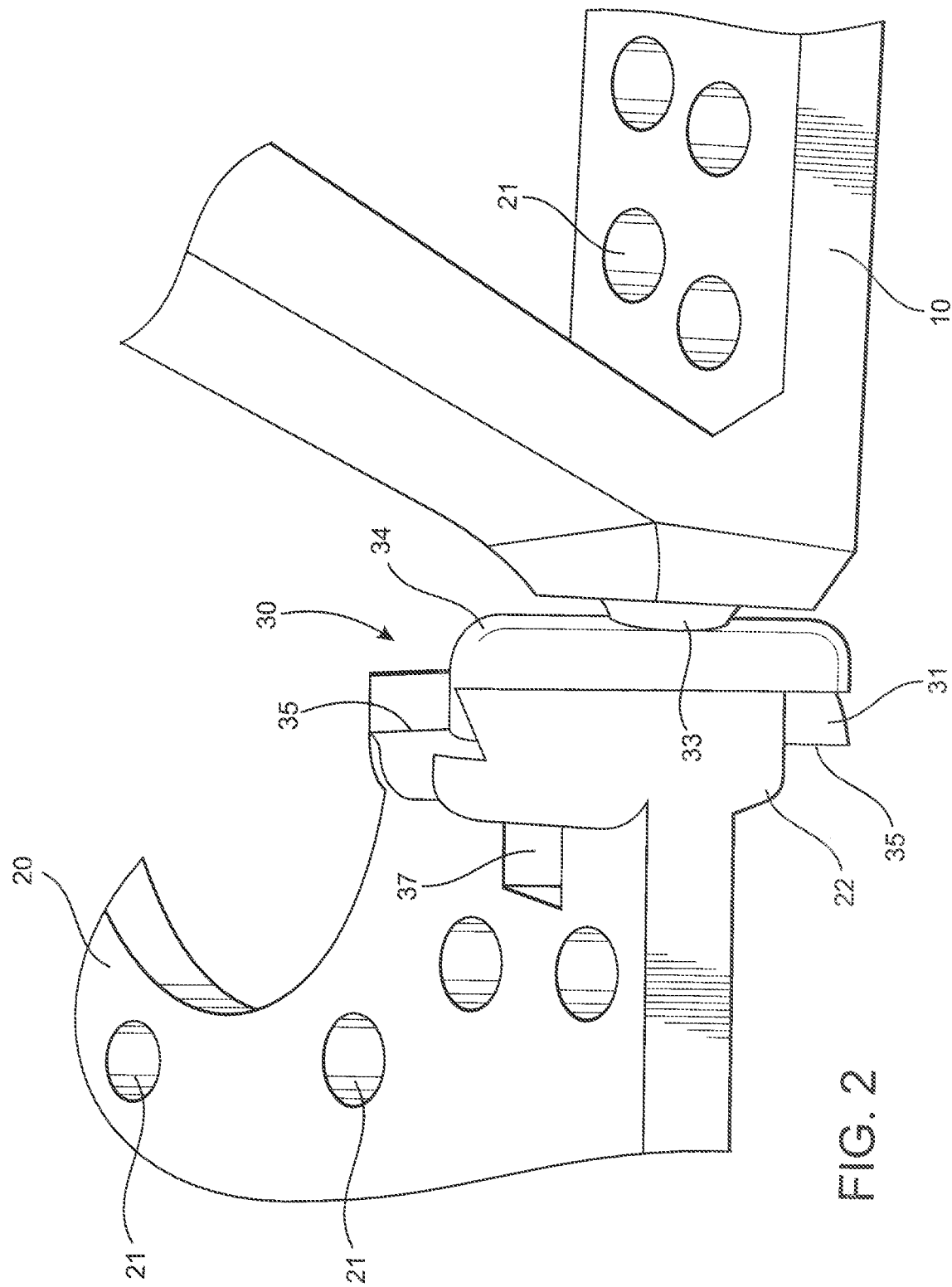
FIG. 2 is a side perspective view in partial cutaway of the joint of the preferred embodiment of FIG. 1.
Figure 3:
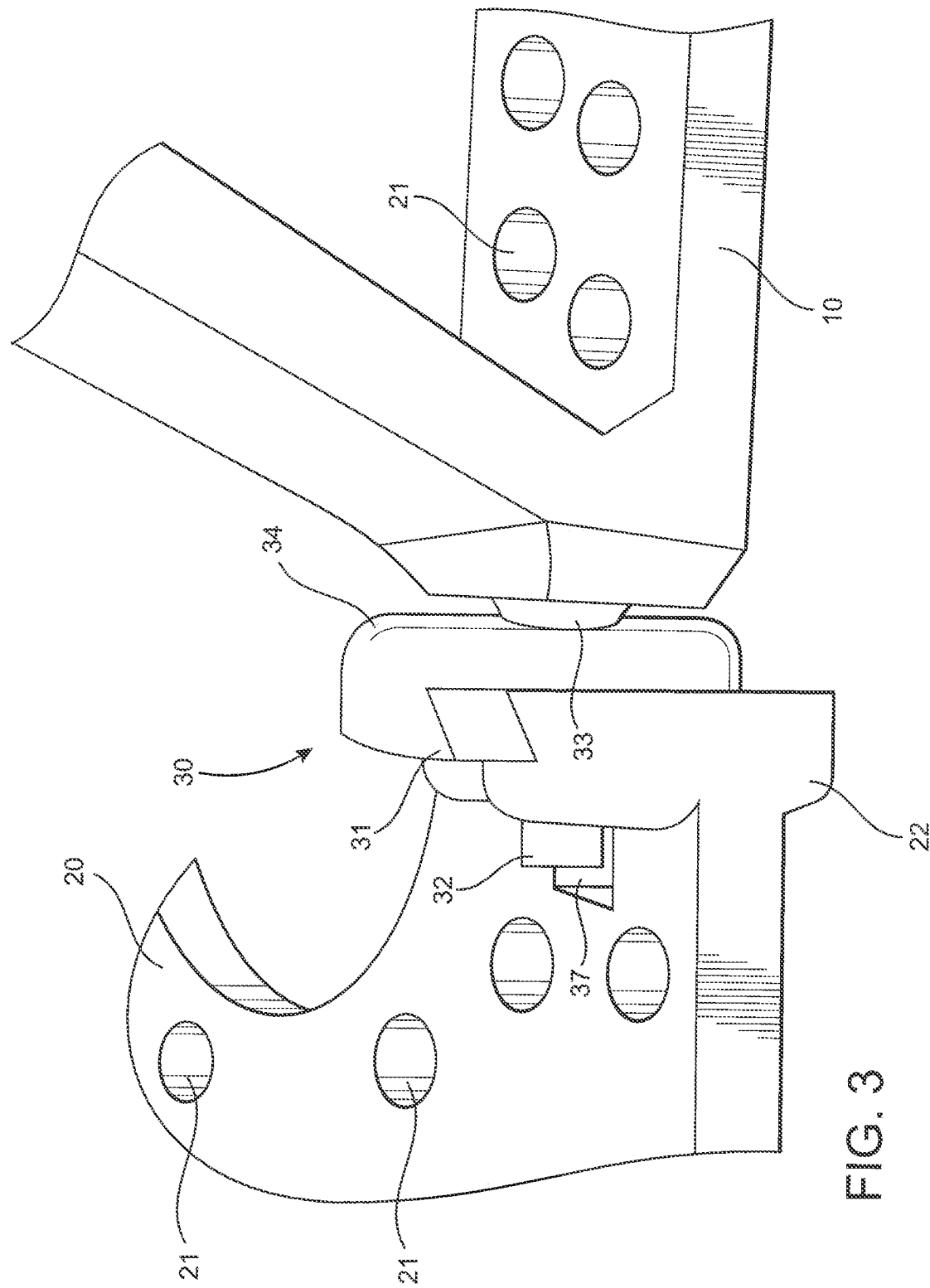
FIG. 3 is a side perspective view in partial cutaway of the joint of the preferred embodiment of FIG. 1.

With primary reference to FIG. 1, the joint 30 as depicted in the preferred embodiment comprises a joint housing 34, an extension element 32, and a pivot element 33. The joint housing 34 can be made of any sufficiently rigid or sturdy material, such as in the depicted embodiment and is preferably centrally apertured to receive the extension element 32, which extends substantially into and, in this case, through the joint housing 34, into an aperture 37 formed in or adjacent to the end 22 of the base 20. In other embodiments, the extension element 32 may only partially recess into the joint housing 34. The joint housing 34, in at least one of the preferred embodiments, may be curvilinear about its circumference, but other suitable geometric configurations will suffice. The joint housing 34 also includes at least one flange 31 extending outwardly in a direction substantially transverse and/or perpendicular to a remainder of the joint housing 34. In addition, the one or more flanges may have an elongated configuration extending at least partially along the height or length of the remainder of the flange housing 34 so as to be disposed adjacent and/or contiguous opposite ends of the flange housing 34, as represented in at least FIGS. 2-5. The flanges 31 facilitate a confronting movable and/or sliding engagement with an adjoining structure which, in the depicted embodiment is the corresponding one of the cooperatively configured and structured ends 22 of the base element 20. However, in at least one alternative embodiment the joint housing 34 and flange 31 may be movably and/or adjustably connected to another part of the dynamic foot plate assembly 1, such as a cooperatively disposed, dimensioned and structured portion and/or corresponding end of the side element 10. The flanges 31 maintain interconnection between the joint housing 34 and the base element 20 while simultaneously facilitating linear movement substantially resembling sliding in the direction of the length and/or height of the of the flanges 31, as depicted in FIGS. 2-5. This sliding, or "vertical" displacement, confers a significant benefit to a medical professional using the dynamic foot plate assembly 1 by allowing the adjustment of the various components of the dynamic foot plate 1 into a desired orientation by varying the disposition of the base element 20 relative to at least one side element 10 both prior to the onset of and during treatment.

Accordingly, the extension element 32 may be a substantially elongated member that extends wholly or substantially through a correspondingly disposed and configured opening or aperture 37 in the end 22 of the base 20. In addition, the extension element 32 extends through and is transversely aligned with the opening 37 and length of the flange 31 into the joint housing 34. The length and dimension of the extension element 32 may resemble a screw, bolt or other threaded rod-like structure capable of extension through or partially through the joint housing 34. The extension element 32 in the preferred embodiment is a threaded elongated member, with the threads extending substantially along the outer length of the extension element 32 and facilitating a frictional confronting and/or threaded engagement with opposing threads lining the interior of the central aperture in the joint housing 34. Therefore, the extension element 32 and the joint housing 34, being interconnected, may reciprocally move transversely to the plane of the base 20. Further, due to the fact that the extension element 32 is connected to the pivot element 33, the one side element 10 also may be selectively disposed relative to the plane of the base 20 such as being raised above the base 20 or disposed below the base 20, relative to the ankle area 100 when the dynamic foot plate 1 is operatively disposed relative to the ankle area 100.

The structure of the extension element 32 allows for the variable disposition or displacement of the base element 20 and at least one side element 10, or alternatively between two side elements 10, directed along the length of the joint housing 34. This is depicted in at least FIGS. 3-5. Variable disposition is achieved by rotation of the extension element 32 about its axis, which can extend or retract the extension element 32 through the joint housing 34, flange 31 and possibly into the aperture 37, via the utilization of the threads extending substantially along the length of the extension element 32. Further, operative positioning of the extension member 32 will be explained in greater detail with regard to the embodiment of FIG. 12.

Figure 4:
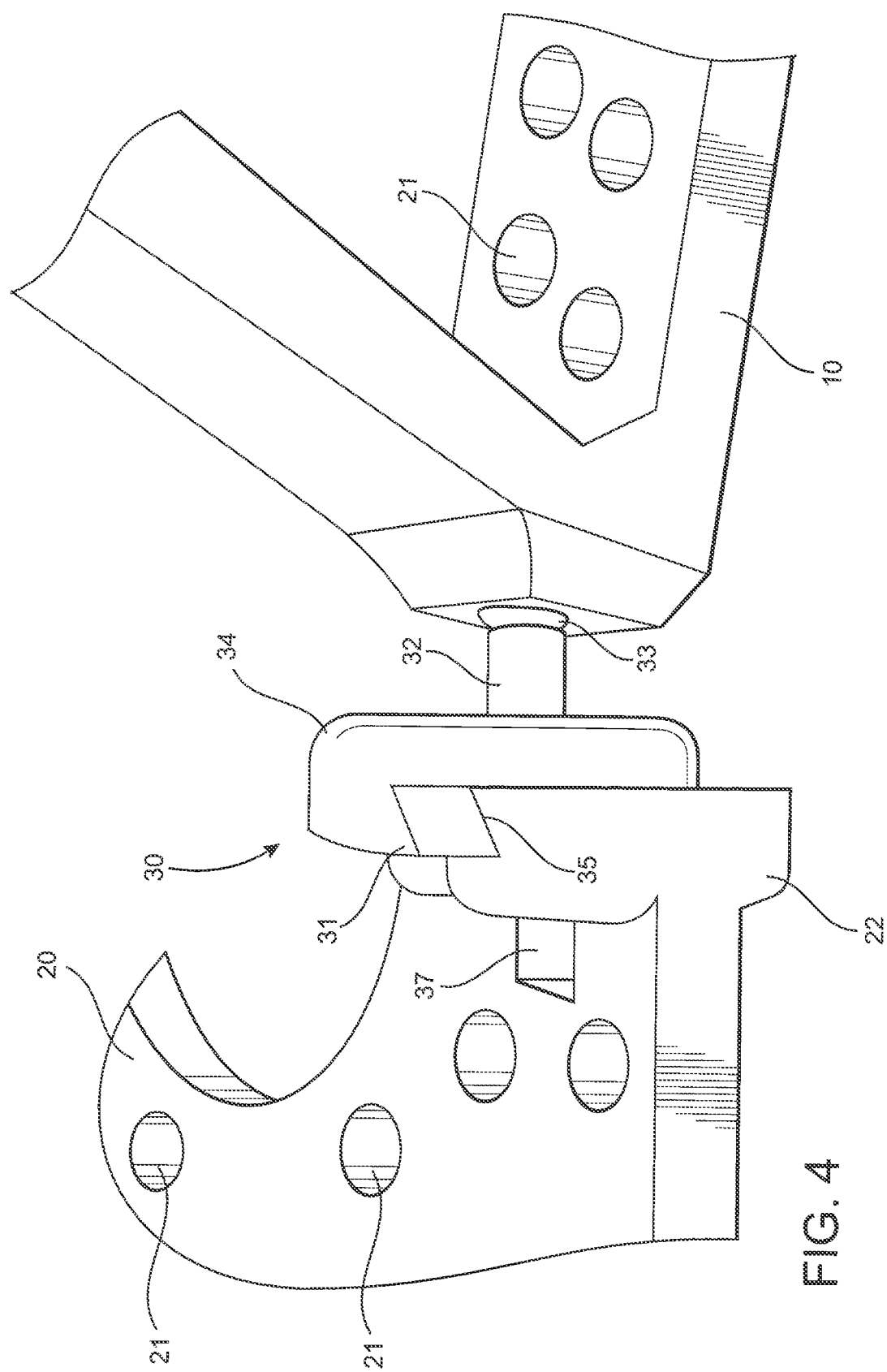
FIG. 4 is a side perspective view in partial cutaway of the joint of the preferred embodiment of FIG. 1.
Figure 5:
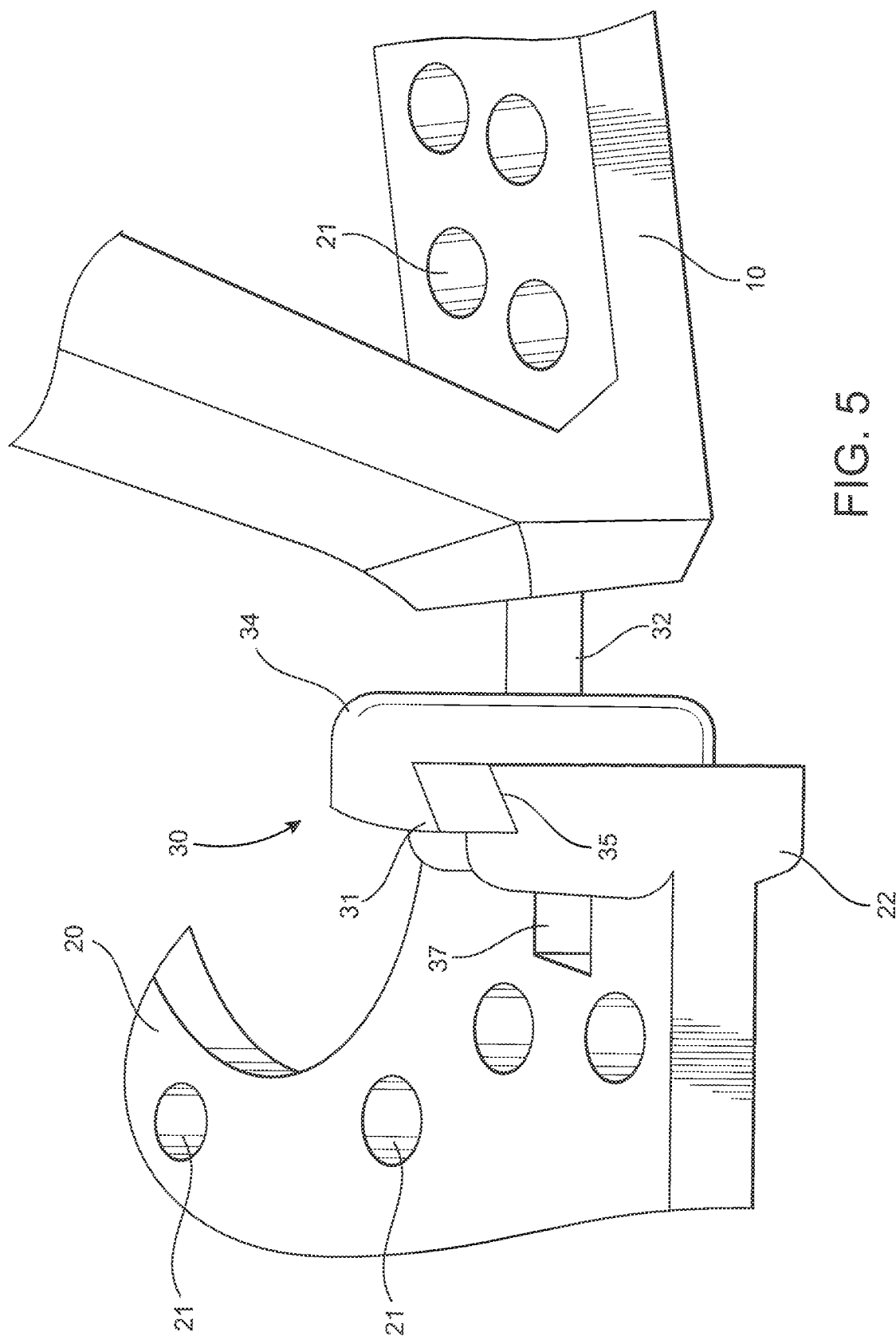
FIG. 5 is a side perspective view in partial cutaway of the joint of the preferred embodiment of FIG. 1.

Attached to the extension element 32 preferably, but not necessarily, at one end of the extension element 32, is a pivot element 33 structured for an at least partially universal range of motion. The pivot element 33 may comprise a ball and socket substantially equivalent structure. The pivot element 33 facilitates a tilting or angularly oriented movement to establish a preferred or predetermined variance of the angular disposition of the axis or length of the side element 10 relative to the base element 10 as depicted in FIGS. 4 and 5. Alternatively, in another embodiment, the joint 30 could be configured to connect two side elements 10, allowing for a similar tilting motion by way of the pivot element 33, disposed in a socket in one of the two side elements 10, to vary the angular disposition of the axes between the two side elements 10. The pivot element 33 also facilitates the relative varying of the disposition of a base element 20 and a side element 10, as shown in the preferred embodiment, or between two side elements 10, in a lateral direction toward or away from the ankle. Finally, the joint 30 may also facilitate a rotational or rotary movement in such a way that does not vary the angular disposition of the base element 20 and side element 10, or as between two side elements 10. Further, the structural and operative features of the joint 30 and its cooperative components comprises movements of a side element 10 with either a base element 20 or another side element 10, facilitated by the pivot element 33, can be a compound movement that includes at least one of the aforementioned tilting, lateral, and/or rotary movements, necessary for a medical professional or other operator to properly dispose a side element 10 into a predetermined orientation relative to the ankle area 100 and base 20 to effect treatment.

Accordingly, the joint 30 including the extension member 32 and pivot member 33, when assuming the structural and operational features as represented in at least FIGS. 1-5 and/or equivalent structure is capable of a variety of different movements and positions being assumed between the base 20 and a corresponding one of the side elements 10. More specifically, the adjustably interconnected side element 10 may move rotationally about the longitudinal axis of the extension member 32; may move angularly upwardly, downwardly, inwardly, outwardly, relative to the ankle area 100 enclosed by the dynamic foot plate assembly 1. In addition, the joint 30, including the joint housing 34 and flange 31 may be disposed, as represented in FIGS. 1-5, either upwardly, or downwardly or in substantial alignment with the plane of the base element 20, as represented in FIG. 1. Further, the provision of the extension member 32 within the joint 30 facilitates a variance in the spacing between (inwardly towards or outwardly away from) the base 20 and/or corresponding end 22 thereof and an end portion of the corresponding side element.

Figure 12:
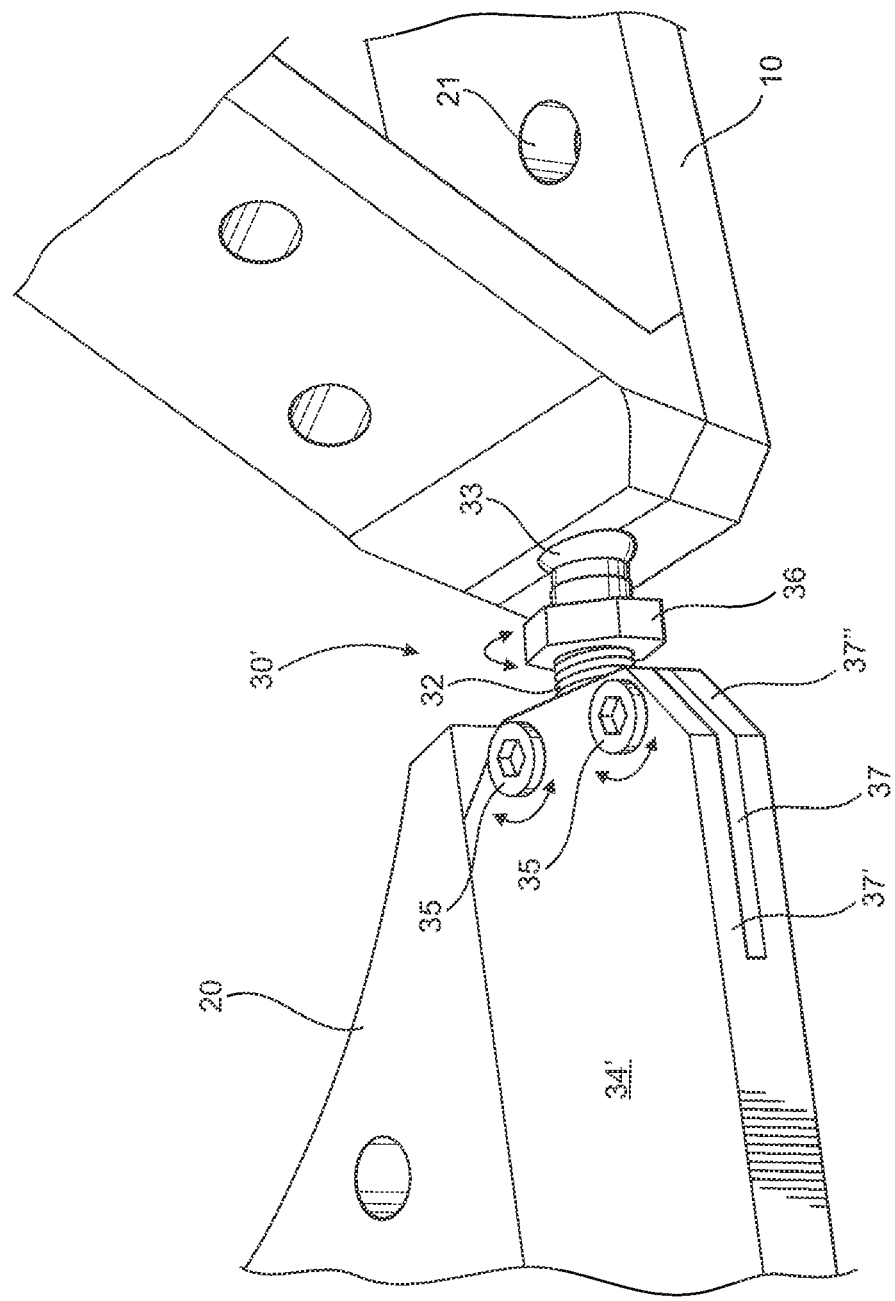
FIG. 12 is a perspective view in partial cutaway of one of a plurality of joints as structured in at least one preferred embodiment of the present invention.

Another embodiment of the joint is given at 30' as shown in FIG. 12. This embodiment may further comprise a nut 36 or similar centrally apertured connector type structure disposed upon the extension element 32 and coaxially aligned therewith. The nut 36 is capable of translation along the extension element 32 and can be placed in confronting engagement with the side element 10. This confronting engagement between the nut 36 and the side element 10 restricts or eliminates the movement of the side element 10 facilitated by the pivot element 33 as described above. Additionally, the joint 30' may comprise an alternate embodiment of a joint housing 34' interconnected to a base element 20 or side element 10. This joint housing 34' may comprise a plurality of bolts, nuts, or other connector or compression elements, represented as 35. These connector or compression elements 35 may be threaded such that a rotational force, such as with a screwdriver, hex key, wrench, etc. is applied about the central axis, the head of any one of the compression elements 35 exerts a compressive force upon the joint housing 34'. The result of the compressive force is to increase the frictional forces exerted upon the extension element 32, causing the extension element 32 to become frictionally locked in a desired orientation. Consequently, the joint housing 34' may be structured in such a way that the frictional force component of the frictional confronting engagement, as previously described, exerted upon the extension element 32 by the joint housing 34' is capable of being varied. One of a possible number of structures is the inclusion of an aperture or gap 37 or similar spacing between two separate parts 37', 37" of the joint housing 34', in which the extension element 32 is disposed. As such, a compressive force exerted by a compression element 35 causes the aperture or gap 37 to decrease in width, resulting in the substantially fixed "clamping" of the extension element 32 there between. Consequently, the two parts 37', 37" of the joint housing 34' are forced together, and in turn increase the compression and thus frictional forces, i.e. clamping forces, exerted upon the extension element 32. Thus, the extension element 32 is sandwiched between the two parts 37', 37", causing the extension element 32 to become frictionally locked or clamped in a desired orientation, which may limit the outward extension or positioning of the extension element and the spacing between the side element 10 and the joint housing 34'. Rotating the compression element or elements 35 in the opposite direction causes the gap 37 to widen, decreasing the aforementioned clamping forces and unlocking the compression element 32, restoring its capability for previously described movement.

Figure 7:
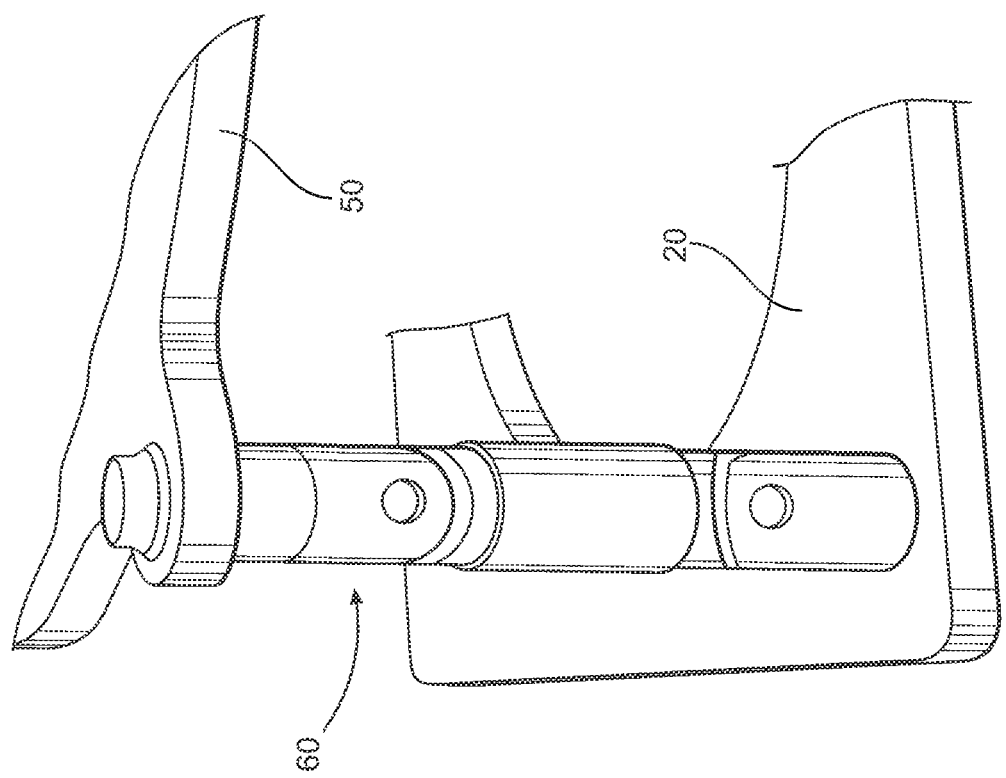
FIG. 7 is a side perspective view in partial cutaway of one of a plurality of strut members as represented in FIG. 7 and which may be operatively associated with the preferred embodiment of FIG. 1.

Additionally, disposed above the base element 20 and at least partially surrounding the ankle is a support member 50, which is depicted in FIGS. 6 and 7. With primary reference to FIG. 6, the support member 50 has a plurality of apertures 21 collectively disposed substantially along its length. The apertures are disposed and structured to facilitate the connection of fixation struts, preferably using fixation bolts, which are known to those practiced in the art and are used to effect treatment of the ankle or lower leg. The support member 50 is preferably, at least partially curvilinear including a configuration that facilitates disposition thereof that at least partially surrounds the ankle area as represented in at least FIGS. 6 and 9-11. At least one strut aperture 51 is present on the support member 50 and extends partway or totally through the support member 50 and allows for attachment of the strut member 60 to the support member 50. The method of attachment of the preferred embodiment and alternatives will be discussed in detail below.

Figure 8:
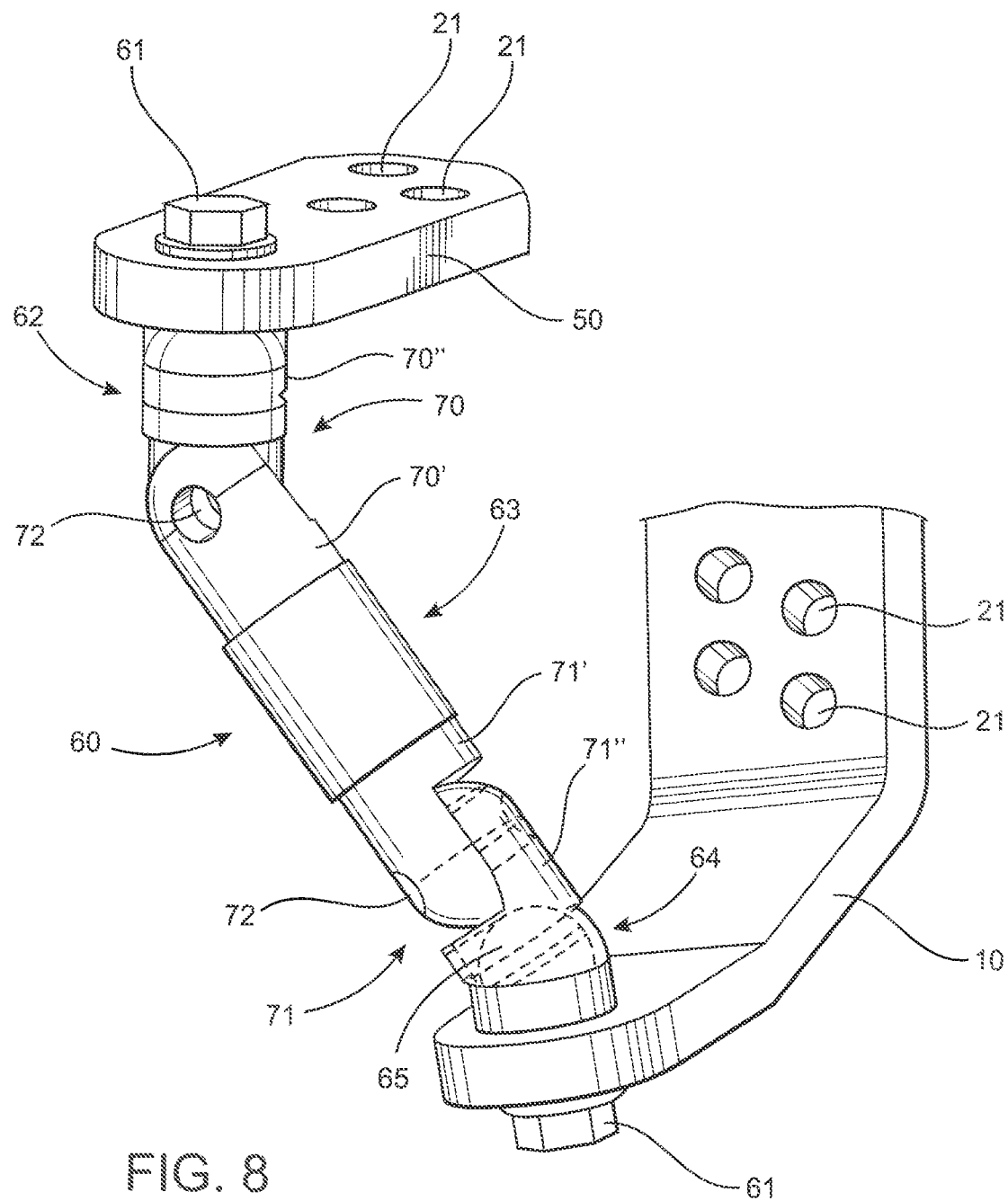
FIG. 8 is a perspective view in partial cutaway of one of a plurality of strut members as represented in FIGS. 6 and 7, with thin lines used for clarity to contrast the depiction of the internal structure of the strut member.

With primary reference to FIG. 8, a strut member 60 comprises a pair of strut attachment elements 61 that attach one end of the strut member 60 to a support member 50 and the opposing end to the side element 10 or, as shown in FIG. 7, a base element 20. With reference to FIGS. 9, 10, and 11, possible alternate embodiments of strut members are given at 60' and 60". Returning to FIG. 8, the strut attachment element 61 can be any means of fixed attachment that allows for confronting engagement between the strut member 60 and the desired attaching element, be it the aforementioned side element 10, base element 20, or support member 50 such as a threaded bolt or suitably strong adhesive substance. As depicted in at least one of the preferred embodiments, the strut attachment element 60 is comprised of a nut that fastens a threaded bolt that passes through an aperture in the desired attaching element to ensure abutment between the attaching element and the strut member 60. The strut member 60 is structured so as to facilitate the variable disposition of the support member 50, a base element 20, and/or a side element 10 relative to the ankle. The strut attachment element 61 that passes through the support member 50 is attached to a first housing 62 and abuts the support member 50. The first housing 62 can be socketed or otherwise structured to receive one end of a first hinge 70, the structure of which will be discussed in detail below. On the opposite end of the first hinge 70 is a second housing 63. The second housing 63 is socketed at either end, or can be centrally apertured, and is structured to receive one end of the first hinge 70 and one end of the second hinge 71 as depicted in FIG. 8. The end of the second hinge 71 is disposed within a third housing 64, which abuts either a base element 20 or a side element 10 in a confronting engagement facilitated by the second of two strut attachment elements 61. Further, the second housing 63 is structured to adjust or vary the length of the strut member 60 upon rotation or other appropriate manipulation thereof. Such a variance in length will be evident or accomplished by a variance of the distance between a primary first hinge member 70' and a secondary first hinge member 70".

The first hinge 70 is comprised of a primary first hinge member 70', a secondary first hinge member 70", and a hinge fastener 72. The secondary first hinge member 70" is disposed with a hollow, socket or other similar recess in the first housing 62 in such a way as to facilitate the rotary motion or disposition between the primary first hinge member 70' and the secondary first hinge member 70". The exposed end of the secondary first hinge member 70" is apertured to receive a hinge fastener 72. Abutting the secondary first hinge member 70" is the primary first hinge member 70', which is similarly apertured as shown in FIG. 8 to receive the hinge fastener 72. The abutting ends of the primary and secondary first hinge members 70' and 70" are cooperatively structured and configured to pivot about a common axis.

Additionally, one of a pair of hinge fasteners 72 joins the primary first hinge member 70' and the secondary first hinge member 70" and facilitates their rotational movement about an axis defined by the central axis of the hinge fastener 72. The hinge fastener 72 can be a bolt and nut or any similar fastening structural composition that allows for tightening to adjust the confrontation between the primary first hinge member 70' and secondary first hinge member 70". By adjusting the confrontation, it is possible to cause the first hinge 70 to become frictionally locked, which is desirable when disposing the dynamic foot plate assembly 1 into a predetermined position for treatment. When the first hinge 70 is frictionally locked, reducing the tensile forces directed along the central axis of the hinge fastener 72 will restore the ability for the primary first hinge member 70' and secondary joint hinge member 70" to rotate about the aforementioned axis. The primary second hinge member 71' and the secondary second hinge member 72" are similarly attached with the second of a pair of hinge fasteners 72, the function of which is substantially the same as set forth above.

Furthermore, a second housing 63, which may be socketed on each end or else centrally apertured, is structured to receive in one end of the primary first hinge member 70' and in the other end the primary second hinge member 71', as shown in FIG. 8. The second housing 63 is structured to interconnect the primary first and second hinge members 70' and 71'. The second housing 63 is further structured to facilitate the rotational movement of the primary first and second hinge members 70' and 71' relative to one another about an axis, defined as the central axis of the second housing 63.

The second hinge 71 comprises the primary second hinge member 71' and a secondary second hinge member 71" cooperatively structured and configured to pivot relative to one another about a common axis, defined as the central axis of the aforementioned hinge fastener 72 that joins the two secondary hinge members 71' and 71".

A third housing 64 is pivotally interconnected to the secondary second hinge member 71", and is structured to facilitate an at least partially universal range of motion of the secondary second hinge member 71", and may substantially resemble a ball in socket 65, as represented.

With primary reference to FIGS. 13-25, another embodiment of the present invention is directed to an adjustable joint assembly. As generally represented in FIGS. 13-16 a housing 100 includes at least one but in certain instances a plurality of joint assemblies 102 and 104. The structural and operational details of each joint assembly 102, 104 are represented in FIGS. 17-23. However, for purposes of clarity, FIGS. 17-23 represent only a single joint assembly 102 or 104, wherein the joint assembly 102 and 104 have common structural and operational features.

More specifically, each joint assembly 102, 104 includes a primary adjustment assembly generally indicated as 106 and a secondary adjustment assembly 108 in addition, each joint assembly includes a lock assembly 110 which, as should be apparent, is at least partially incorporated within and defined by common structural components of the secondary adjustment assembly 108. Further, each primary adjustment assembly 106 includes an adjustment member 112 and a base 114. Further the primary adjustment assembly 106 includes a first gear 116 connected to and movable with the adjustment member 112. As set forth above FIGS. 17 through 21 represent a single joint assembly 102 and/or 104. However, as disclosed in FIGS. 13-16 a plurality of the joint assemblies 102 and 104 may be incorporated within the same housing 100. As such, a preferred relative positioning of the joint assemblies 102 and 104 is in substantially perpendicular relation to one another. Accordingly, each joint assembly 102, 104 includes a separate, individual adjustment member 112 (see FIGS. 13-16) and each of the joint assemblies 102 and 104 are operatively connected to a common base 114.

Additional structural and operative features include the common base 114 preferably having and at least partially spherical configuration and/or substantially ball shape and a connecting or mounting stem 117 connected thereto and movable therewith. The stem 117 may or may not be threaded, as represented but is structurally adapted for attachment to a strut 60' or other component to which the one or more joint assemblies 102 and/or 104 are adjustably connected. The primary adjustment assembly 106 is movably and/or adjustably connected to the base 114 by a cam assembly. More specifically, the cam assembly includes one or a plurality of cam members 118 mounted on and movable with the common base 114. The cam assembly also includes a race or drive member/structure 120 connected directly to the adjustment member 112 and movable therewith, as will be explained. It is again emphasized that when a plurality of joint assemblies 102 and 104 are concurrently operable with a common base 114, each includes an adjustment member 112 having a race 120 which interact to the extent that the race 120 drivingly engages a separate one of the plurality of cam members 118. Accordingly, interaction between the race 120 and corresponding one of the cam members 118 movably interconnect the adjustment member 112, of each joint assembly 102, 104, to the common base 114 and connected component/strut 60'.

Figure 21:
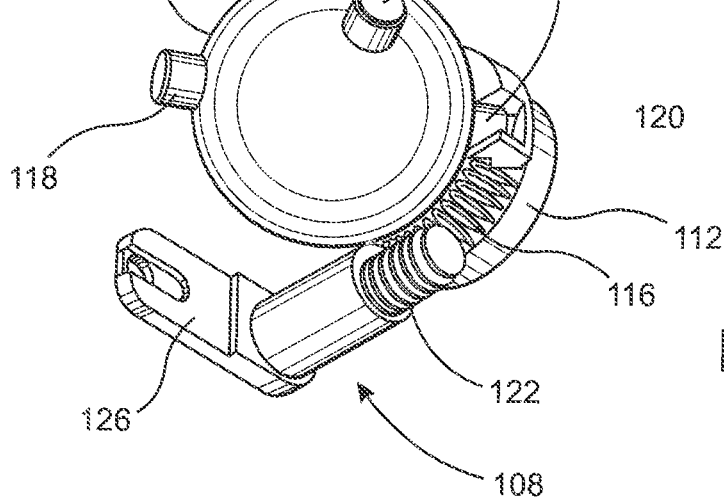
FIG. 21 is a perspective view in detail of the embodiment of FIG. 17-20 in a movement restricting orientation.
Figure 22:
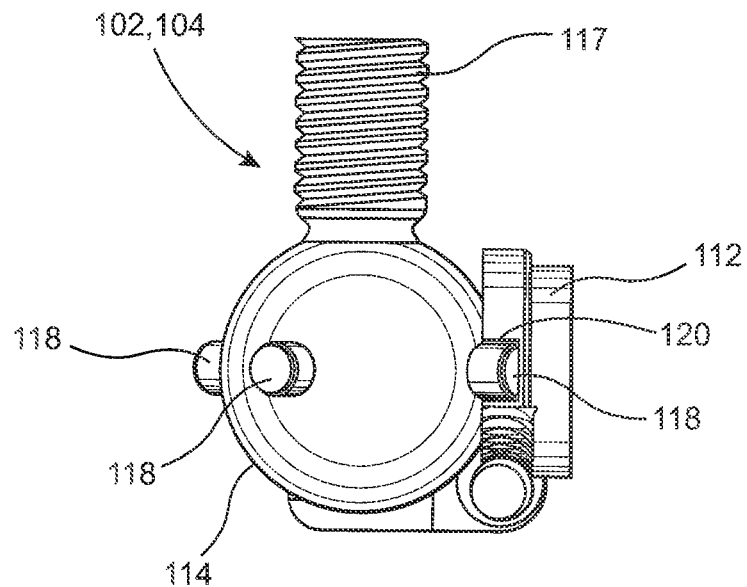
FIG. 22 is a rearview of the embodiment of FIG. 21.
Figure 22A:
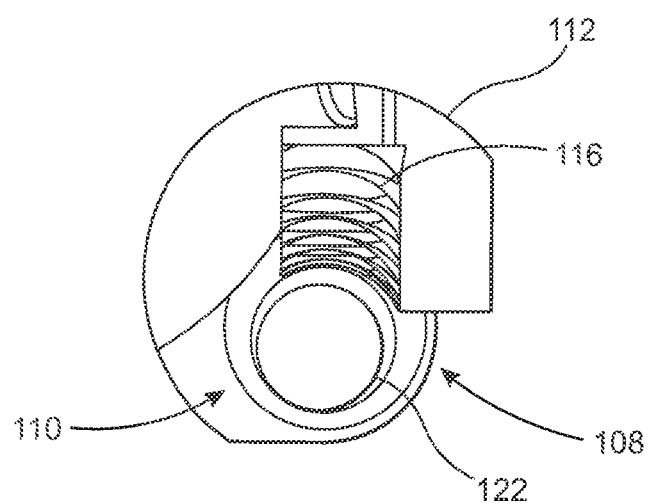
FIG. 22A is a detail view in schematic form of the indicated portion of FIG. 22.

As generally indicated above, the secondary adjustment assembly 108 is integrated with the lock assembly 110 and as such the secondary adjustment assembly 108 and the lock assembly 110 include common structural components. More specifically, the secondary adjustment assembly 108 and lock assembly 110 include a second gear 122 mounted in a sleeve or housing 124 and rotatable therein. Further, a positioning lever or handle 126 is connected to the sleeve or housing 124 and is structured to position the lock assembly 110 into and out of "movement restricting relation" to the primary adjustment assembly 106. In more specific terms, the movement restricting relation between the lock assembly 110 and the primary adjustment assembly 106 is at least partially defined by the second gear 122 moving into meshing engagement with the first gear 116. Such movement is accomplished by physically positioning the lever 126 from the "open position" represented in FIGS. 17 and 18A into a "closed position" as represented in FIGS. 21 and 22A.

Figure 18:
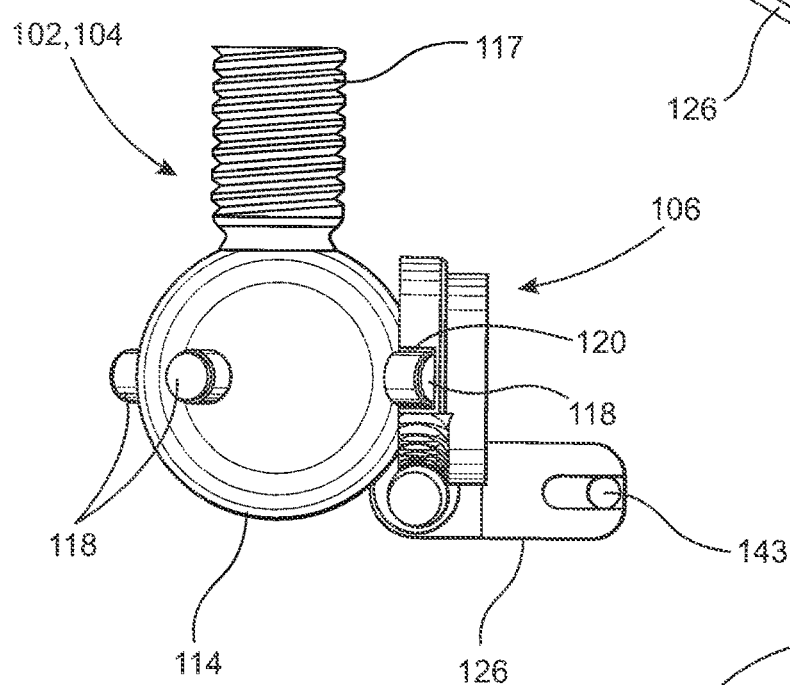
FIG. 18 is a rear view of the embodiment of FIG. 17.
Figure 18A:
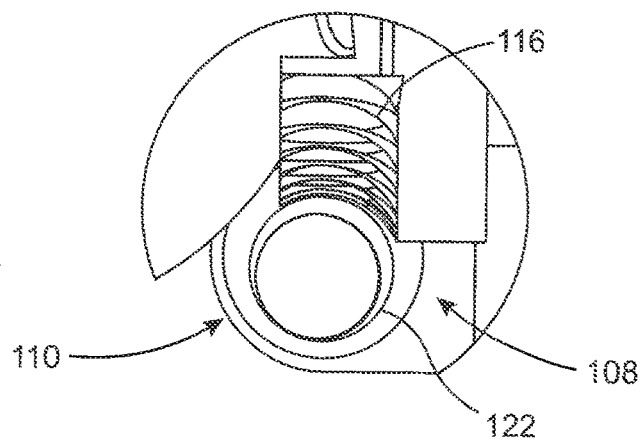
FIG. 18A is a detail view in schematic form of the indicated portion of FIG. 18.
Figure 19:
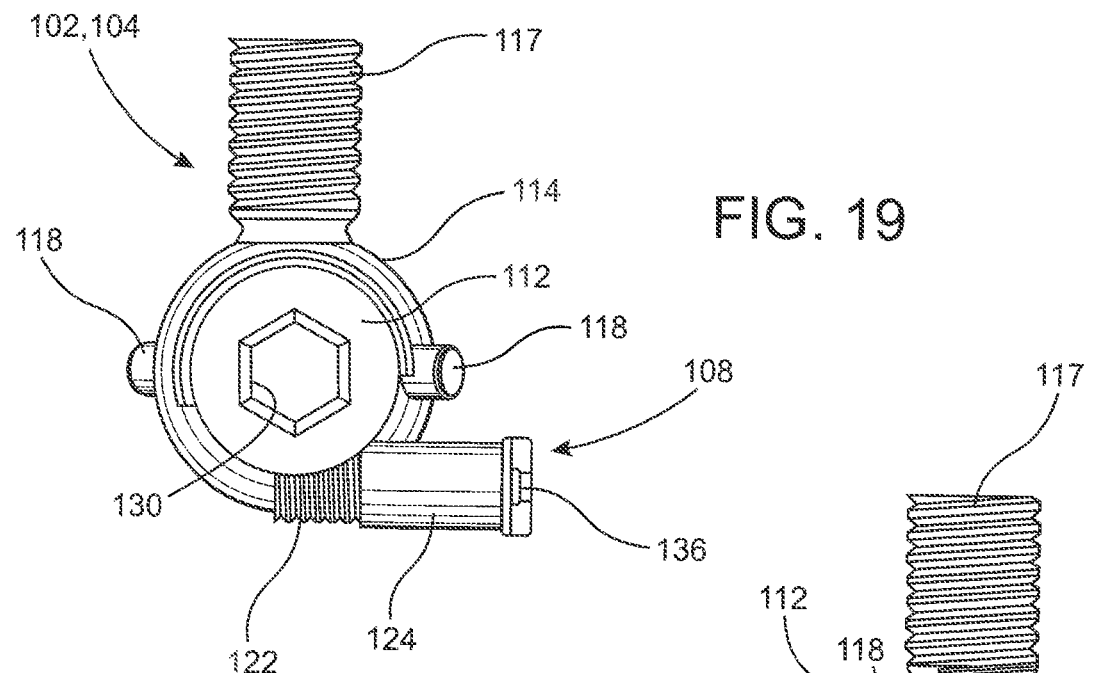
FIG. 19 is a front view of the embodiment of FIGS. 17 and 18.
Figure 20:
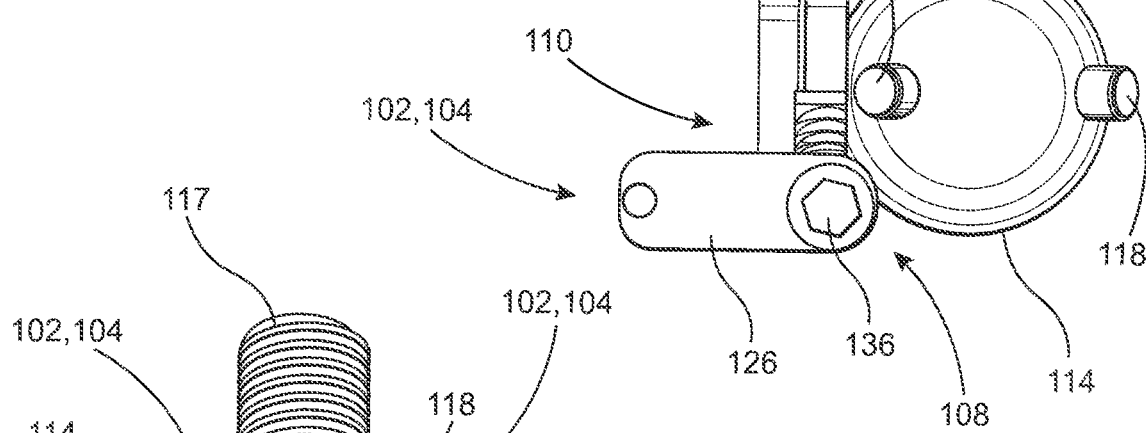
FIG. 20 is a side view of the embodiment of FIGS. 17-19.

As clearly represented in FIG. 18A, the second gear 122 is disposed out of meshing engagement with the first gear 116. As a result the primary adjustment assembly 106 and more specifically the adjustment member 112 is allowed to rotate for purposes of positioning the stem 117 and corresponding component or strut 60' through a first range of motion, which is more specifically defined by a gross adjustment mode, as will be explained with primary reference to FIG. 14. However and with reference to FIGS. 21-22A, when the lever 126 is rotated or otherwise disposed into the "closed" position, the second gear 122 is brought into meshing engagement with the first gear 116 of the adjustment member 112. The positioning of the lever 126 between the "open position" and the "closed position" will be explained in greater detail hereinafter with primary reference to FIGS. 23 and 24. When the lever 126 is in the "closed position" as represented in at least FIGS. 21 and 22A, rotation of the adjustment member 112 of the primary adjustment assembly 106 will be restricted, if not completely prevented, due to the meshing engagement of the second gear 122 with the first gear 116. Therefore movement of the base 114, stem 117 and connected component or strut 60' will be restricted from passing through the aforementioned "first range of motion" or "gross adjustment mode", by a manipulation of the adjustment member 112.

However, due to the fact that the second gear 122 is in meshing engagement with the first gear 116, proper manipulation and/or rotation of the second adjustment assembly 108 and the second gear 122, as will be explained in greater detail with primary reference to FIGS. 16 and 25, will result in a rotational driving engagement of the second gear 122 with the first gear 116. The rotation of the second gear 122 will result in a driven rotation of the first gear 116, causing an interaction between the corresponding cam member 118 and race 120. Such interaction of the camming assembly will cause the base 114 to pass through a "second lesser range of motion", which is defined herein as the "fine adjustment mode".

Further for purposes of clarity and as used herein, the term "gross adjustment mode" and "fine adjustment mode" respectively refer, at least in part, to a major "gross" adjustable positioning and minor "fine" adjustable positioning, respectively, of the strut 60' or other component to which the base 114 is connected. As such, the gross adjustment mode refers to greater first range of motion of the strut 60' or component so as to accommodate the assembly, initial positioning, alignment, etc. of the various components of the external fixator, such as relative to the foot plate assembly 1. In contrast, the "fine adjustment mode" refers to a smaller or lesser, second range of motion through which the strut 60' or component may be adjustably disposed. Moreover, the fine adjustment mode may be used to accomplish a more precise position or orientation of the strut 60' or component, once the external fixator has been assembled and initially positioned on the patient, but perhaps not perfectly or preferably oriented.

Figure 14:
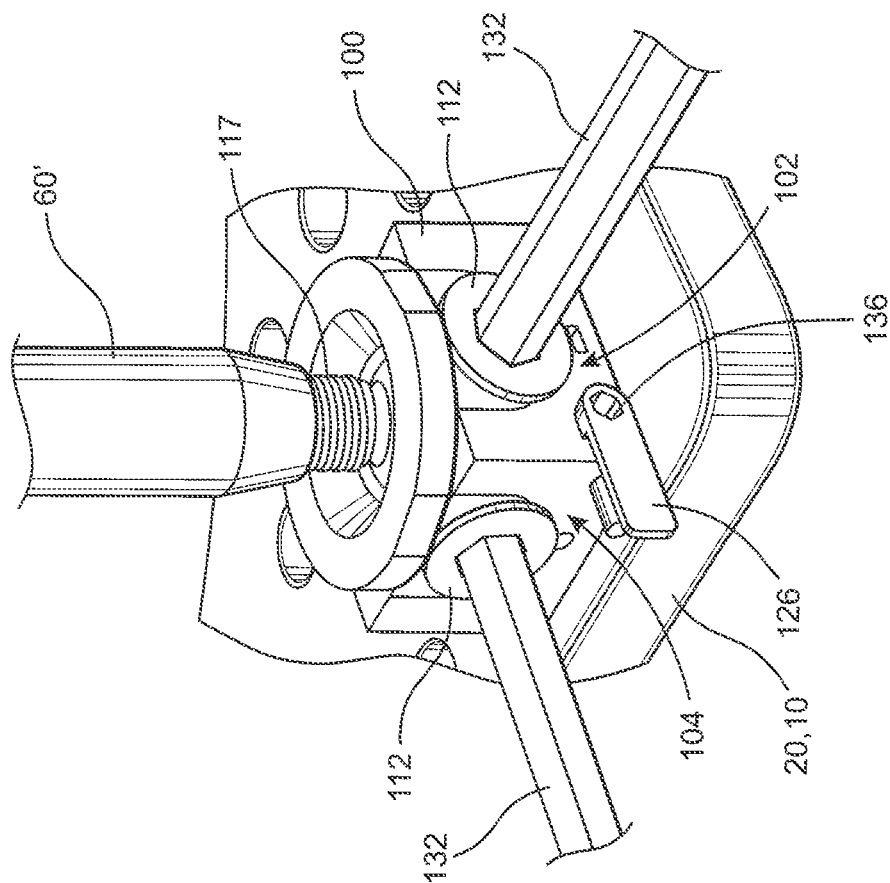
FIG. 14 is a perspective view of the embodiment of FIG. 13 in a different stage of operation.
Figure 13:
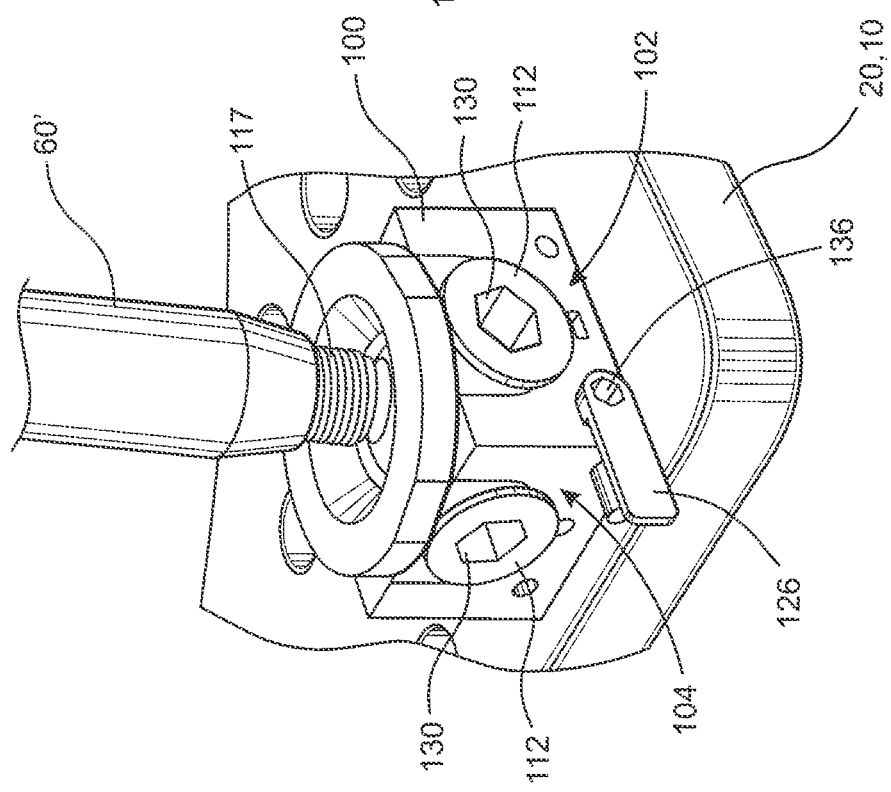
FIG. 13 is a perspective view of an adjustable joint assembly representing one preferred embodiment of the present invention.

Selective and manual movement/rotation of the adjustment member 112 of the primary adjustment assembly 106, through the first range of motion, is accomplished when the lever 126 and lock assembly 110 is in the open position as represented in FIGS. 13, 14 and 17-18A. In addition, an opening and/or channel 130 is formed in an outer, exposed face or portion of the adjustment member 112. This opening or channel is dimensioned and configured to correspond to and receive a tool 132 therein. The tool 132 may be manually rotated in opposite directions, which in turn will result in interaction and driving engagement of the race 120 of the adjustment member 112 with a corresponding cam 118. As a result, the base 114, as well as the strut or component 60' connected to the stem 117, will move through the greater/larger first range of motion and thereby be grossly adjusted. Further, due to the fact that the base 114 may have a ball shape as well as the interaction between the race 120 and the corresponding cam 118, the first range of motion will comprise an at least partial universal range of motion. As also represented in FIG. 14, a plurality of joint assemblies 102, 104 associated with a common housing 100 may be concurrently adjusted and concurrently move through the gross adjustment mode due to the fact that the base 114 is common to both the adjustment members 112 of both joint assemblies 102 and 104 and interacts there with through corresponding ones of the cam assemblies. Therefore, two tools 132 may be concurrently manipulated and/or reciprocally rotated to accomplish the at least partial universal range of motion and gross adjustment mode of the connected strut or component 60'.

Figure 16:
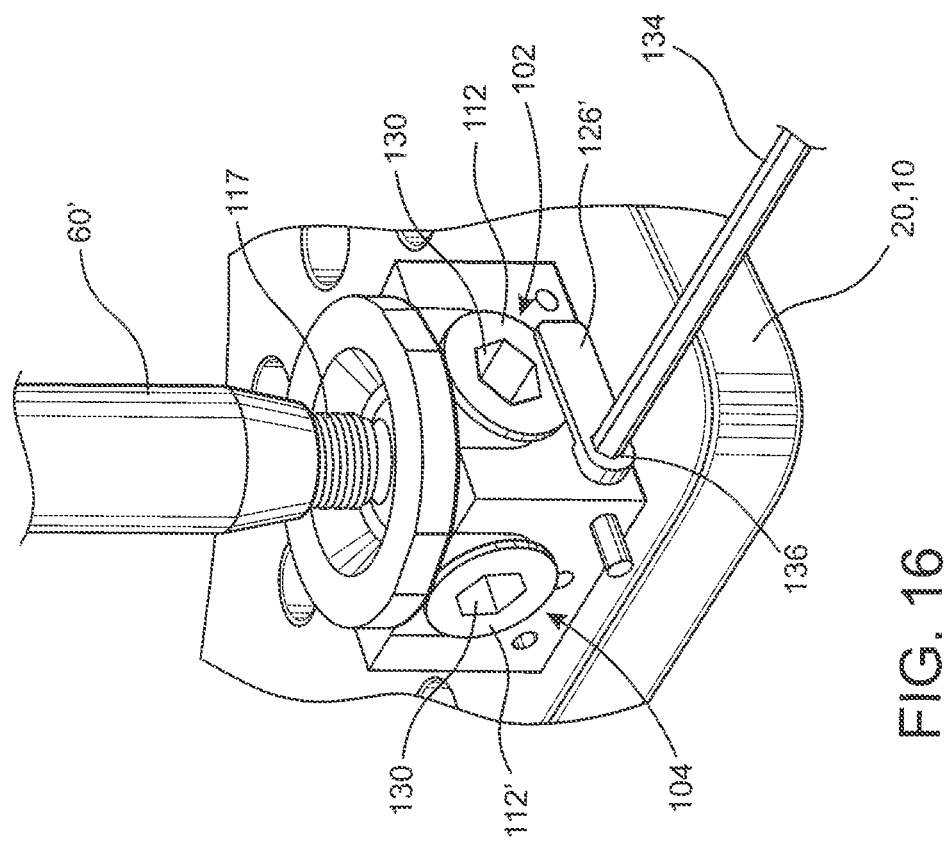
FIG. 16 is a perspective views of the embodiment of FIGS. 13-15, in a different stage of operation.
Figure 15:
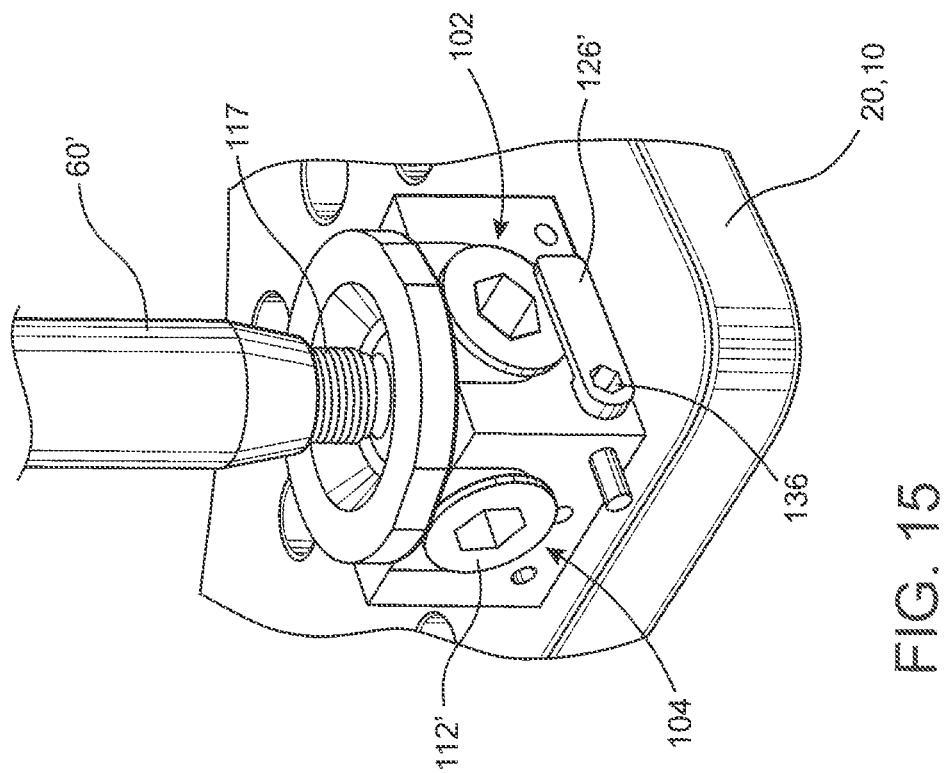
FIG. 15 is a perspective view of the embodiment of FIGS. 13 and 14 in a different stage of operation.
Figure 17:
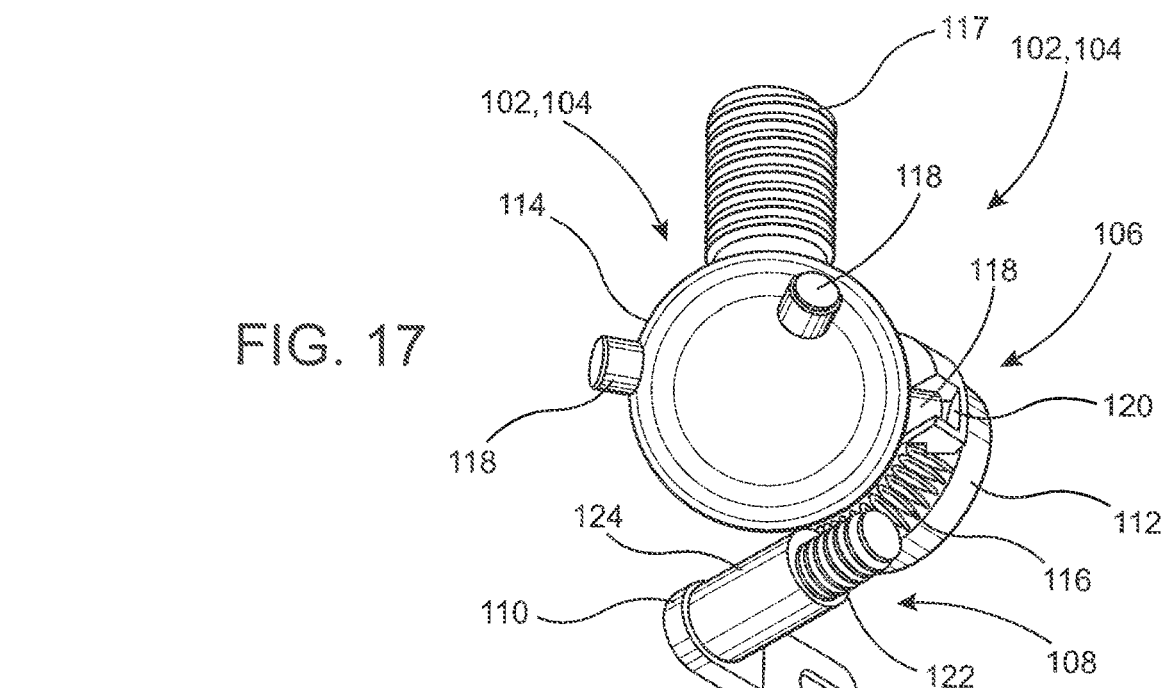
FIG. 17 is a perspective view in detail of the operative components of at least a portion of the adjustable joint assembly of the embodiment of FIGS. 13-16.
Figure 24:
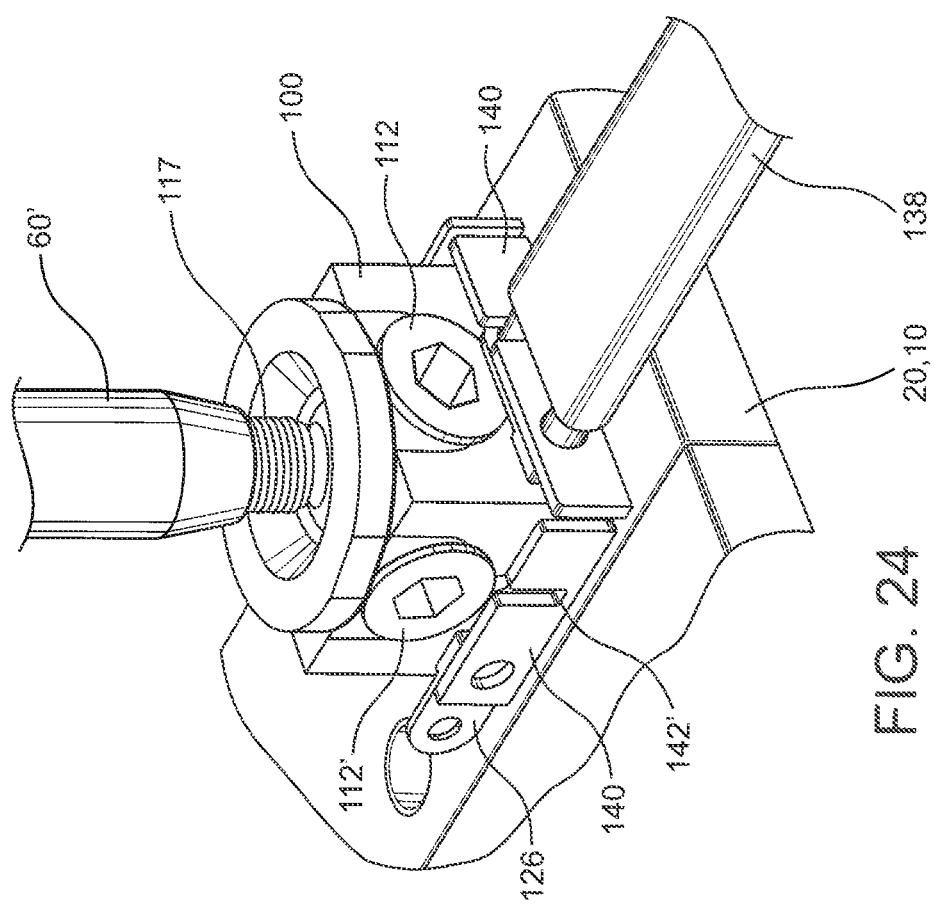
FIG. 24 is a perspective view of the embodiment of FIG. 23 in a different stage of operation.
Figure 23:
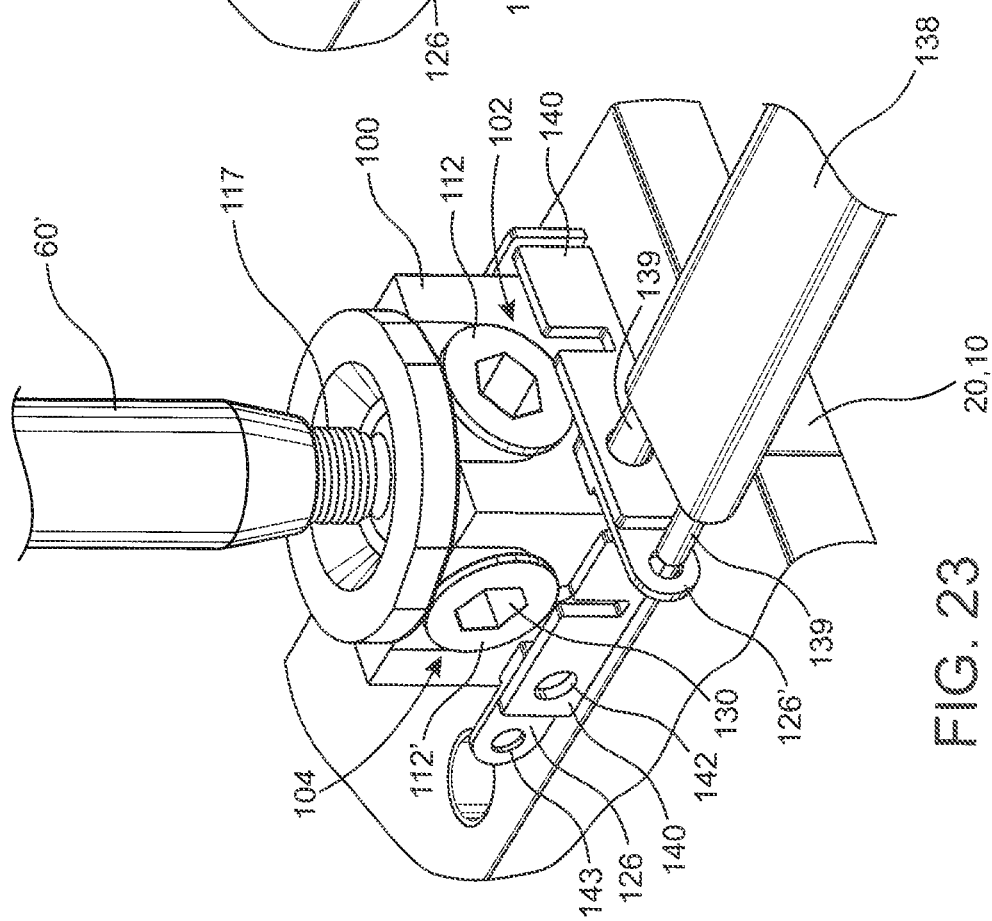
FIG. 23 is a perspective view in fully assembled form of the embodiment of FIGS. 13-16 of the adjustable joint assembly of the present invention.
Figure 25:
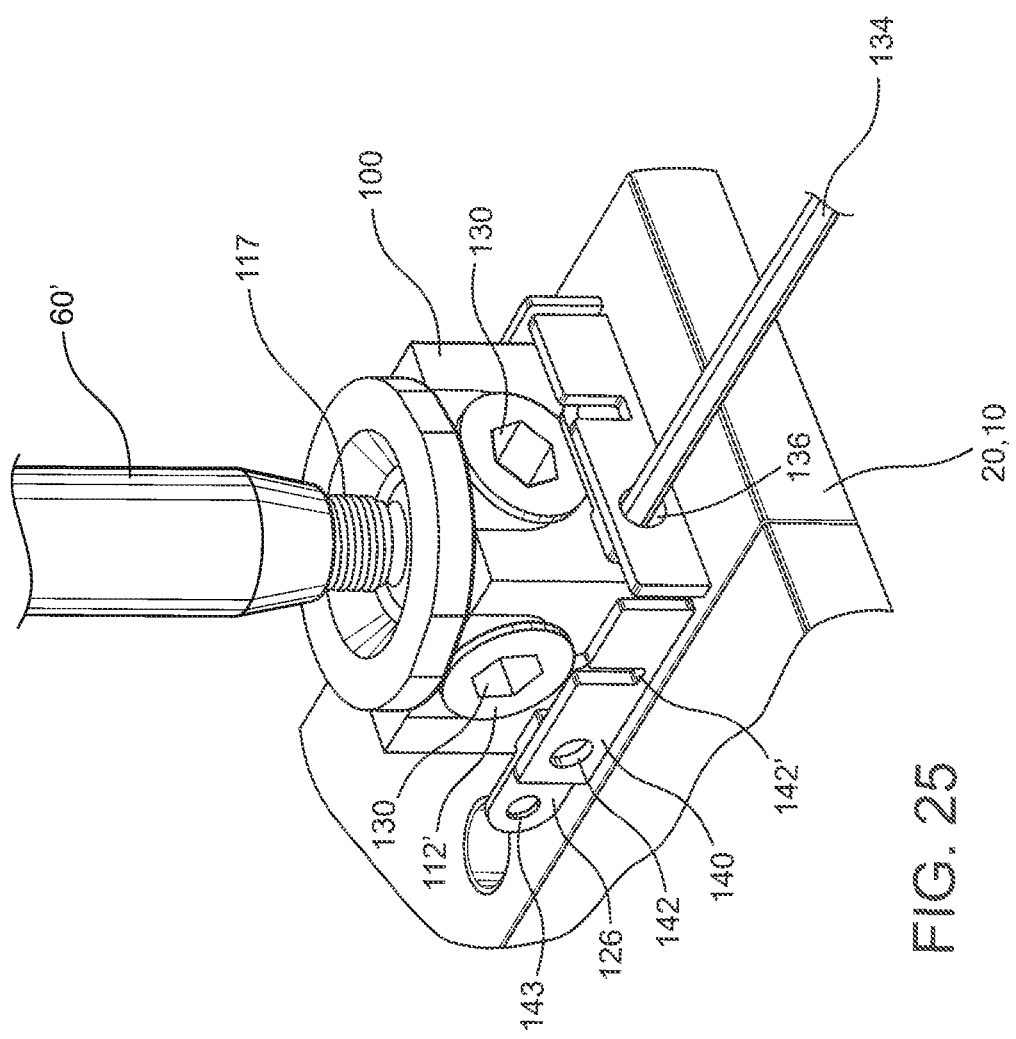
FIG. 25 is a perspective view of the embodiment of FIGS. 23 and 24 in a different stage of operation.

With primary reference to FIGS. 15 and 16 and as also at least partially represented in FIGS. 23-25, accomplishment of the fine adjustment mode of the connected component or strut 60' is accomplished by moving the lever 126 into the "closed position" as represented. Such movement will position the second gear 122 into meshing engagement with a correspondingly positioned first gear 116, thereby preventing or at least restricting the movement of the adjustment member 112, such as by use of a tool 132. However, due to the fact that the second gear 122 is in fact in meshed, engagement with a correspondingly disposed first gear 116, rotation of the second gear 122 will serve to forcibly rotate the first gear 116 through the use of an appropriately sized and dimension tool 134. Moreover, the exposed end or portion of the lock assembly 110 and/or second adjustment assembly 108 includes an opening or channel 136. The opening or channel 136 is correspondingly dimensioned and configured to receive the tool 134 therein. Therefore, rotation of the tool 134 will cause a rotation of the second gear 122, such as relative to the sleeve 124. The meshing engagement between the second gear 122 and a correspondingly positioned first gear 116, will thereby result in a forced rotation of the corresponding first gear 116, and interaction between the race 120 and the corresponding cam 118 and movement of the base 114 and component 60' connected to the stem 117, through the lesser, second range of motion and "fine adjustment mode".

With primary reference to FIGS. 23-25, yet another structural modification and/or embodiment of the present invention includes an exterior shield or a plurality of shield segments 140 disposed in overlying at least partially surrounding relation to the levers 126 of each of the lock assemblies 110 associated with each of the joint assemblies 102 and 104. Each of the shield or shield segments 140 include an appropriately positioned number of openings and/or apertures 142 and 142' to facilitate the pivotal or rotational placement of corresponding ones of the levers 126 from the open position as represented in FIG. 23 into the closed position as represented in FIG. 24. Such positioning may best be accomplished by an appropriate additional positioning tool 138 having outwardly extending fingers or like structures 139 disposed, dimensioned and configured to pass through openings 142 and 142' as well as an additional opening or aperture 143 formed and a distal or free end of each of the levers 126. Once inserted in the position represented in FIG. 23, the positioning tool 138 is pivoted or rotated through an arc of approximately 180° so as to dispose the lever 126 from the open position of FIG. 23 into the closed position of FIGS. 24 and 25 as also represented in FIGS. 15 and 16. Once the lever 126 is disposed into the closed position, the tool 134 is inserted through the opening 136 associated with the second adjustment assembly 108, the lock assembly 110 and the second gear 122, as described with reference to FIGS. 15 and 16. Rotation of the tool 134 in the manner described will rotate the corresponding second gear 122 and serve to adjust the strut 60' through the lesser second range of motion and fine adjustment mode. As should be apparent, the positioning tool 138 will be used to dispose the lever 126 back into the open position of FIG. 23.

To further clarify the structural and operational features of the one or more joint assemblies 102, 104 of the present invention an overall comparison should be made between the structures of the embodiments of FIGS. 17-22A and FIGS. 23-25. More specifically, the structures of FIGS. 17-22A, as set forth above, represent the structural components of a single joint assembly 102 and/or 104. As such, the lock assembly 110 and integrated $2^{nd}$ adjustment assembly 108 include the corresponding $2^{nd}$ gear 122 disposed in substantially aligned and/or substantially parallel relation to the plane of the adjustment member 112 and associated first gear 116.

Therefore, and again for purposes of clarity, as represented in FIGS. 23-25, it is emphasized that the lever 126' and the corresponding $2^{nd}$ gear 122 structurally associated therewith is operative with the joint assembly 104 to drive and/or rotate the adjustment member 112'. In cooperation there with, the lever 126, is structurally associated with the corresponding lock assembly 110 and $2^{nd}$ adjust assembly 108 and when in its closed position is operative to drive and or rotate the first gear 116 associated with the adjustment member 112 of the joint assembly 102.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A joint assembly usable on an external fixator device and structured to position a component through different adjustment modes, said joint assembly comprising:
    a primary adjustment assembly connected in adjusting relation to the component and including a first gear,
    said primary adjustment assembly comprising a base and an adjustment member, the component connected to the base and movable therewith,
    said primary adjustment assembly further comprising a cam assembly disposed in movable interconnecting relation between said base and said adjustment member,
    forced movement of said adjustment member defining a forced movement of said base and the component, through a first range of motion, via said cam assembly,
    a secondary adjustment assembly structured to movably adjust the component through a second range of motion and including a second gear,
    said primary adjustment assembly disposed in movably interconnecting relation between said secondary adjustment assembly and the component,
    a lock assembly at least partially incorporated in said secondary adjustment assembly and positionable into and out of movement restricting relation to said primary adjustment assembly,
    said movement restricting relation at least partially defined by said second gear disposed in meshed, movement restricting engagement with said first gear,
    said first range of motion representative of a gross adjustment mode of the component and said second range of motion representative of a fine adjustment mode of the component, and
    said base comprising a ball shape, said first range of motion further comprising an at least partially universal range of motion.

2. The joint assembly as recited in claim 1 wherein said fine adjustment mode comprises said second gear disposed in meshed, driving engagement with said first gear.

3. The joint assembly as recited in claim 1 wherein said lock assembly is at least partially defined by said second gear.

4. The joint assembly as recited in claim 1 wherein said cam assembly comprises at least one cam member mounted on said base and movable therewith and a race member mounted on said adjustment member in driving engagement with said one cam member.

5. The joint assembly as recited in claim 4 wherein rotation of said adjustment member is determinative of disposition of said base, via interaction between said cam member and said race, through said first range of motion.

6. The joint assembly is recited in claim 1 wherein driving, meshing engagement of said second gear with said first gear comprises said second range of motion and said fine adjustment mode of the component.

7. The joint assembly is recited in claim 1 further comprising said first gear movable with said adjustment member, said second gear movable with and relative to said first gear and said adjustment member.

8. The joint assembly is recited in claim 1 wherein said second gear is rotationally mounted on said lock assembly and rotational, driving engagement of said second gear with said first gear at least partially defines said second range of motion and said fine adjustment mode of the component.

9. A plurality of joint assemblies usable on an external fixator device and each structured to position a component through different adjustment modes, each of said joint assemblies comprising:
 a housing including a plurality of primary adjustment assemblies and a plurality of secondary adjustment assemblies movably disposed on said housing,
 each of said plurality of primary adjustment assemblies including a common base, an adjustment member and a cam assembly, each of said cam assemblies disposed in movable interconnecting relation between said base and corresponding ones of said adjustment members,
 wherein forced movement of each of said adjustment members defines a forced movement of said base and the component, via corresponding ones of said cam assemblies, through a first range of motion,
 said base comprising a ball configuration and said first range of motion comprising an at least partially universal range of motion,
 each of said plurality of primary adjustment assemblies disposed in movably interconnecting relation between a different one of said plurality of secondary adjustment assemblies and the component,
 each of said adjustment members comprises a first gear movable therewith; each of said plurality of secondary adjustment assemblies defining at least a portion of a corresponding one of a plurality of lock assemblies and including a second gear;
 each of said second gears movable into and out of mating engagement with corresponding ones of said first gear; driving engagement of each of said second gears with corresponding ones of said first gears comprising a second range of motion of said component, and
 said first range of motion representative of a gross adjustment mode of the component and said second range of motion representative of a fine adjustment mode of the component.

10. The joint assemblies as recited in claim 9 wherein each of said cam assemblies comprises at least one cam member mounted on said base and movable therewith and a race member mounted on corresponding ones of said adjustment members in driving engagement with said at least one cam member.

11. The joint assemblies as recited in claim 10 wherein rotation of each of said adjustment members is determinative of disposition of said base, via interaction of corresponding ones of said cam members and said races, through said first range of motion.

12. The joint assemblies as recited in claim 9 wherein mating engagement between each of said second gears and corresponding ones of said first gears defines a movement restricting relation of each of said plurality of lock assemblies with corresponding ones of said adjustment members and the component.

13. The joint assemblies as recited in claim 12 wherein driving engagement of each of said second gears with corresponding ones of said first gears comprises said second range of motion and said fine adjustment mode.

14. The joint assemblies as recited in claim 9 wherein each of said first gears is movable with corresponding ones of said adjustment members, each of said second gears movable with and relative to corresponding ones of said first gears and said adjustment members.

15. The joint assemblies as recited in claim 14 wherein each of said second gears is rotationally mounted on corresponding ones of said lock assemblies; rotational, driving engagement of each of said second gears with corresponding ones of said first gears at least partially defining said second range of motion and the said fine adjustment mode.

* * * * *